(12) United States Patent
Barr et al.

(10) Patent No.: US 11,179,506 B2
(45) Date of Patent: Nov. 23, 2021

(54) NEGATIVE PRESSURE WOUND THERAPY PUMP AND CANISTER

(71) Applicant: CORK MEDICAL, LLC, Indianapolis, IN (US)

(72) Inventors: Aaron Barr, Fishers, IN (US); John Anthony Lamper, Markleville, IN (US); Philip Leighton Ramge, Indianapolis, IN (US); Elliott Conrad Lasher, Woodmere, NY (US)

(73) Assignee: Cork Medical, LLC, Indianapolis, IN (US)

( * ) Notice: Subject to any disclaimer, the term of this patent is extended or adjusted under 35 U.S.C. 154(b) by 747 days.

(21) Appl. No.: 14/678,493

(22) Filed: Apr. 3, 2015

(65) Prior Publication Data

US 2016/0250398 A1 Sep. 1, 2016

Related U.S. Application Data

(60) Provisional application No. 62/121,961, filed on Feb. 27, 2015.

(51) Int. Cl.
A61M 1/00 (2006.01)

(52) U.S. Cl.
CPC ........ A61M 1/0023 (2013.01); A61M 1/0001 (2013.01); A61M 1/80 (2021.05); A61M 1/90 (2021.05)

(58) Field of Classification Search
CPC .............. A61M 1/0088; A61M 1/0023; A61M 1/0001; A61M 27/00; A61M 1/90
See application file for complete search history.

(56) References Cited

U.S. PATENT DOCUMENTS

| | | | | |
|---|---|---|---|---|
| 5,928,177 A | * | 7/1999 | Brugger | A61M 1/10 604/6.11 |
| 2003/0028156 A1 | * | 2/2003 | Juliar | A61M 39/10 604/310 |
| 2007/0051007 A1 | * | 3/2007 | Reets | F26B 21/002 34/86 |
| 2008/0215029 A1 | * | 9/2008 | Rake | A61M 5/148 604/408 |
| 2011/0098652 A1 | * | 4/2011 | Hasted | A61M 5/14248 604/174 |
| 2012/0289914 A1 | * | 11/2012 | Eckstein | A61M 1/0092 604/313 |
| 2015/0025482 A1 | * | 1/2015 | Begin | A61M 1/0088 604/318 |

OTHER PUBLICATIONS

Definition of "interface," https://www.merriam-webster.com/dictionary/interface, accessed Dec. 19, 2020, captured Apr. 5, 2013. (Year: 2013).*

* cited by examiner

Primary Examiner — Ariana Zimbouski
(74) Attorney, Agent, or Firm — Faegre Drinker Biddle & Reath LLP

(57) ABSTRACT

An apparatus is including a negative pressure wound therapy pump including a pump housing; and a negative pressure wound therapy canister attached to and readily removable from the pump housing; the canister including a flexible conduit; the canister operable to receive suction generated by the pump; the flexible conduit sized, shaped, and located to interface with the pump housing of the pump such that suction produced by the pump is transmitted to the canister via the flexible conduit.

7 Claims, 24 Drawing Sheets

NEGATIVE PRESSURE WOUND THERAPY PUMP AND CANISTER

PRIORITY

This application is a non-provisional application that claims the priority of and incorporates the disclosure of U.S. Provisional Application 62/121,961 filed Feb. 27, 2015.

FIELD OF THE DISCLOSURE

The present disclosure is related to negative pressure pumps and canisters, providing negative pressure wound therapy and to methods of creating the same. The present disclosure is more specifically directed to negative pressure pumps and canisters having a secure coupling that provides for easy mounting and dismounting therebetween while providing a resilient and reliable interface for transfer of negative pressure therebetween.

BACKGROUND

Negative pressure wound therapy, also known as vacuum drainage or closed-suction drainage is a generally accepted medical treatment for tissue wounds. A vacuum source is connected to a wound dressing. Various porous dressings comprising gauze, felts, foams, beads and/or fibers can be used in conjunction with a cover and a controlled vacuum source. The negative pressure operates to draw out fluid from the wound and increases blood flow to the area. Such treatment promotes healing.

DETAILED DESCRIPTION

Briefly, in one example, an apparatus is provided including a negative pressure wound therapy pump including a pump housing; and a negative pressure wound therapy canister attached to and readily removable from the pump housing; the canister including a flexible conduit; the canister operable to receive suction generated by the pump; the flexible conduit sized, shaped, and located to interface with the pump housing of the pump such that suction produced by the pump is transmitted to the canister via the flexible conduit.

In another example, an apparatus is provided including a negative pressure wound therapy pump portion including a pump housing; the pump housing defining a first hinge portion on a first lateral side, the pump housing further defining a latch catch on a second lateral side opposite the first side, the pump portion including a vacuum pump disposed within the pump housing; and a canister sized and shaped to be coupled to and readily removable from the pump portion, the canister including a second hinge portion operable to interface with the first hinge portion, the canister further including a latch sized and shaped to engage the latch catch.

In yet another example, an apparatus is provided including a negative pressure wound therapy canister having a first lateral side, a second lateral side, a front side, and a rear side cooperating to define an interior void; a first hinge portion coupled to the first lateral side, the first hinge portion sized to removably couple to a second hinge portion of a negative pressure wound therapy pump housing; a latch formed on the second lateral side, the latch sized and shaped to selectively engage a latch catch of a negative pressure wound therapy pump housing; and a flexible conduit in fluid communication with the interior void of the canister, the flexible conduit sized and positioned to abut a negative pressure wound therapy pump housing and to transmit suction from the negative pressure wound therapy pump to the interior void of the canister.

Figure 1:
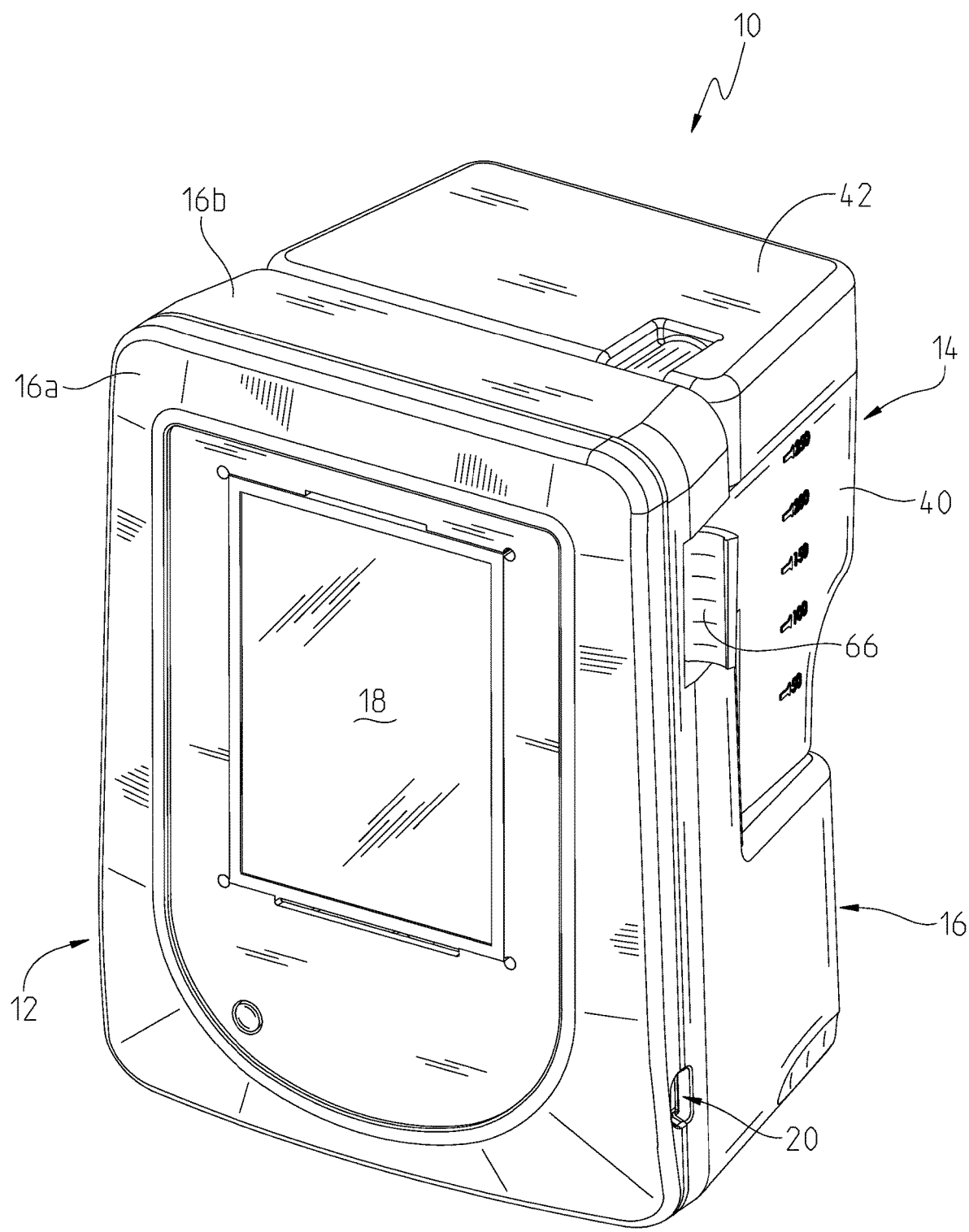
FIG. 1 is a perspective view of a combination pump and first embodiment canister of the present disclosure.

Turning now to the drawings wherein like numerals represent like components, FIG. 1 is a view of exemplary negative pressure wound care device 10. Negative pressure wound care device 10 includes negative pressure wound care pump apparatus 12 and negative pressure wound care canister 14, 14'.

Pump apparatus 12 includes housing 16a,b, screen 18, interface 20, controller (not shown), and pump (not shown). Housing 16a,b includes front housing 16a and rear housing 16b, each constructed from plastic (Acrylonitrile butadiene styrene (ABS)). Front housing 16a includes a void that receives an outer portion of screen 18.

Rear housing 16b couples to front housing 16a to provide an enclosure for screen 18, interface 20, the controller, and the pump. It should be appreciated that at least screen 18 and interface 20 are at least partially exposed to the exterior of housing 16 such that they are readily accessible when apparatus 12 is assembled. Rear housing 16b further includes integrated hinge pin 22 at a first lateral side of the rear thereof. Hinge pin 22 is illustratively a substantially cylindrical element that extends off of the balance of rear housing 16b. Hinge pin 22 illustratively includes a solid forward-facing wall 24 and then includes hollowed-out portions 26 and support ribs 28.

Rear housing 16b further includes cut-out portion 82 proximate hinge pin 22 that provides clearance to allow a hinge knuckle portion 50 of canister 14, 14' to removably couple to hinge pin 22 as described further below. Forward-facing wall 24 of hinge pin 22 extends distally from the balance of the rear housing 16b to such a length as necessary to continue to engage knuckle portion 50 when canister 14, 14' is coupled to housing 16. Also, while the embodiments herein are described having hinge pin 22 being part of housing 16 and having hinge knuckle portion 50 as part of canister 14, 14' embodiments are envisioned where these parts are reversed.

Rear housing 16b further includes latch catch 30 at a rear lateral side opposite hinge pin 22. Latch catch 30 is defined in a lateral side of rear housing 16b and is exposed to the rear thereof. Latch catch 30 includes shoulder 32 that operates to selectively receive and retain a portion of a latch 52 of canister 14, 14'.

Rear housing 16b further includes pump output port (suction port) 34 defined in conduit seat 36. Conduit seat 36 is a frusto-conically shaped member that has output port 34 defined centrally therein. Conduit seat 36 is located in an upper rear corner of rear housing 16b. Conduit seat 36 is located in the upper corner near the lateral side that includes latch catch 30. Output port 34 is coupled to the pump (not shown) within housing 16 such that the output of the pump (suction) is transmitted to output port 34. The largest diameter of conduit seat 36 is illustratively equal to, or slightly different (larger or smaller) than the inner diameter of a tubular conduit 54 of canister 14, 14' as will be discussed below.

Screen 18 is illustratively a touchscreen suitable for receiving input from a user and for displaying information regarding the operation of apparatus 12. Interface 20 is illustratively a USB interface suitable for facilitating communication with the controller located within housing 16. As previously noted, the pump is also located within housing 16 and is controlled by the controller.

Wound canister 14 and wound canister 14' are substantially similar except that canister 14 is designed to have a capacity of 250 mL and canister 14' is designed to have a capacity of 500 mL. Each of canister 14, 14' includes well 40, lid 42, membrane 44, membrane key 46, dam 48, and tubular conduit 54.

Well 40 of both canister 14 and 14' includes hinge knuckle portion 50 at a front of a first lateral side thereof. Well 40 of both canister 14 and 14' further integrally includes latch 52 at the front of a second lateral side thereof that is opposite the first lateral side. As previously noted, well 40 of the two canister sizes 14, 14' differ only in the amount of matter that they are designed to hold. Well 40 includes an input port 56 near a rear corner that is on the same side as hinge knuckle portion 50 and opposite latch 52. Input port 56 is sized, shaped, and located to couple to tubing that is able to be coupled to negative pressure wound care dressings (not shown).

Knuckle portion 50 includes a straight portion 58 that extends laterally and a curved portion 60 that curves forward. In the illustrative example, curved portion 60 is curved about a point to have an inner radius of 0.15 inches. The illustrated curved portion 60 extends approximately 165-degrees. Curved portion 60 is less than a full circle (360-degrees), and less than even a half circle (180-degrees) yet greater than 90-degrees. As will be discussed herein, extending less than a full circle (and less than 180-degrees) provides for ready removal of canister 14 when desired. Further, extending greater than 90-degrees causes a portion of an inner surface of curved portion 60 to engage a forward facing portion of wall 24 of hinge pin 22 such that knuckle portion 50 can be selectively retained on hinge pin 22.

Latch 52 extends in a forward direction and a lateral direction from a front corner of well 40 of canister 14, 14'. The interface of latch 52 and well wall 62 illustratively includes an area of decreased thickness 61 so as to provide flexibility at that point. Latch 52 further includes shoulder 64 and release 66. Shoulder 64 is sized, shaped, and located to engage shoulder 32 of latch catch 30. Release 66 is a portion that provides a lever arm such that pressure applied thereto disengages shoulder 64 from shoulder 32 of latch catch 30.

Lid 42, 42' are differently sized to accommodate the differently sized wells of canisters 14, 14' but membrane 44, membrane key 46, dam 48, and tubular conduit 54 are all common to both canister 14 and canister 14'. Lids 42, 42' include pressure pathway 68 defined by integral walls 70. Pressure pathway 68 extends from suction input 72 through keyway portion 74 and then is exposed to a portion of lid 42 that forms a upper boundary of well 40. As will be discussed herein, various portions, including the shape of pressure pathway (and membrane 44 among others) contribute to decrease the likelihood that any liquid or waste received in well 40 is able to exit canister 14, 14' at suction input 72.

Keyway portion 74 receives membrane 44 that is shaped to be received therein. Membrane 44 is illustratively a hydrophobic membrane that permits air flow therethrough while resisting fluid or solid flow therethrough. More specifically, membrane 44 is illustratively an Oleophobic ePTFE membrane Laminate such as that marketed with a part number QP950 sold by Clarcor under the tradename of ASPIRE. The membrane is illustratively 7.5 mil thick.

Once membrane 44 is positioned within keyway portion 74, membrane key 46 is placed within keyway portion 74 to "sandwich" membrane 44 between membrane key 46 and lid 42. Membrane key 46 is then sonically welded into place in the keyway portion. Dam 48 is then paced over pressure pathway 68 such that a wall of dam 48 engages the edges of the walls of pressure pathway 68. When in place, dam 48 is spaced apart from membrane key 46 such that air passing through membrane 44 and membrane key 46 is able to enter pressure pathway 68. Once positioned, dam 48 is sonically welded into place. This fixation of dam 48 creates a bounded volume of pressure pathway 68 such that any air pulled from suction input 72 traverses pressure pathway 68 and entered pressure pathway 68 by crossing through membrane 44.

Tubular conduit 54 is located within lid 42, 42', is fixed thereto and operates as suction input 72. Tubular conduit 54 is illustratively PVC tubing having an 3/16" ID, a 3/8" OD and 5/8" in length. Tubular conduit 54 is thus flexible/pliable. Tubular conduit 54, at a proximal end 80, mounts to a nipple formed in lid 42, 42' and is illustratively fixed thereto. The nipple includes a pathway therein that is fluidly coupled to and/or part of pressure pathway 68. Accordingly, the lumen of tubular conduit becomes part of pressure pathway 68. Distal end 78 of tubular conduit 54 is generally co-planar with an outer wall 76 of lid 42, 42'. In some embodiments, distal end 78 extends slightly beyond outer wall 76. The exact relative position of distal end 78 is not critical so long as tubular conduit 54 is able to reliably seal to conduit seat 36 and transmit suction to canister 14, 14' when canister 14, 14' is assembled to pump apparatus 12.

Figure 2A:
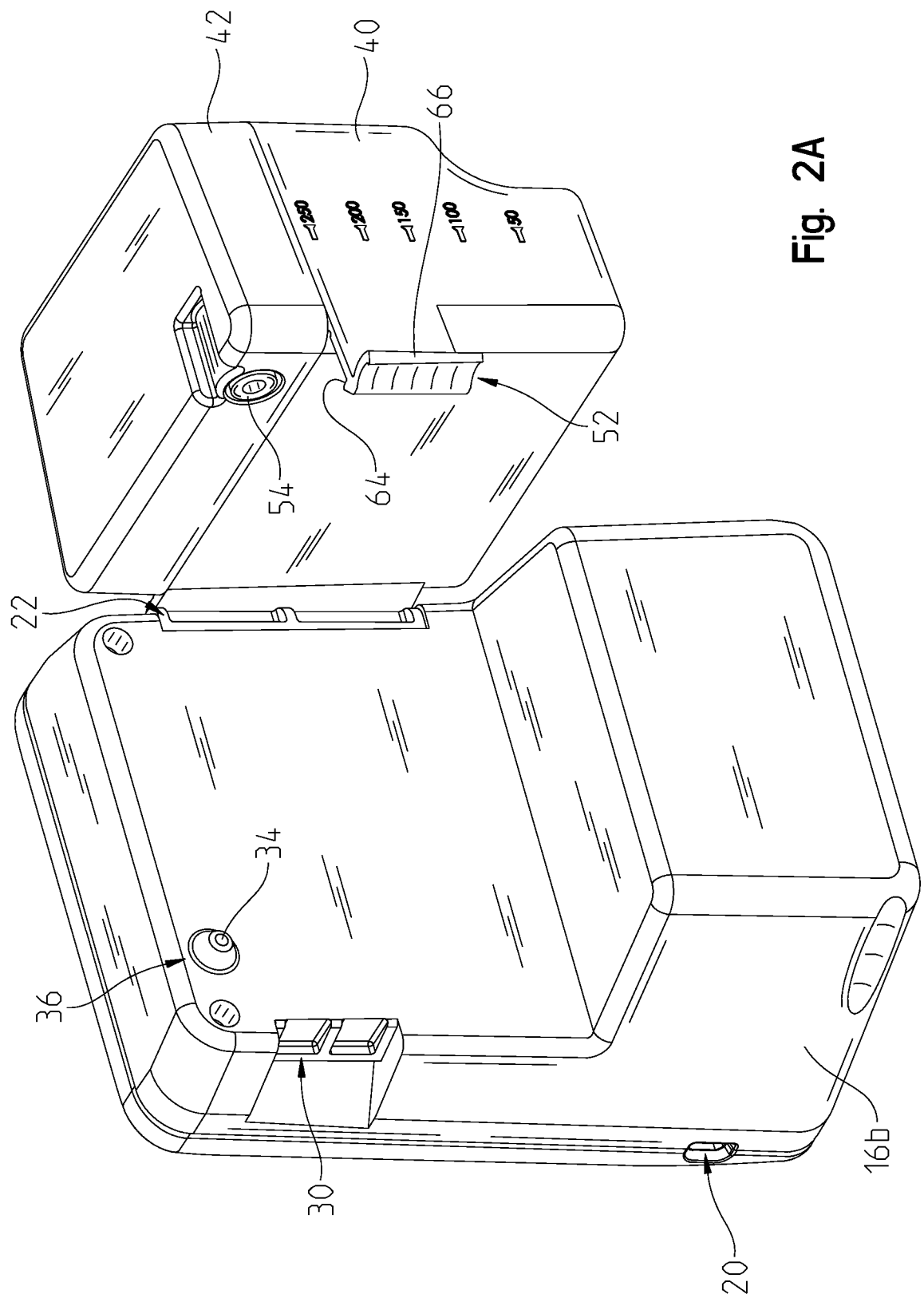
FIGS. 2A-G are perspective views of the pump and canister of FIG. 1.
Figure 2B:
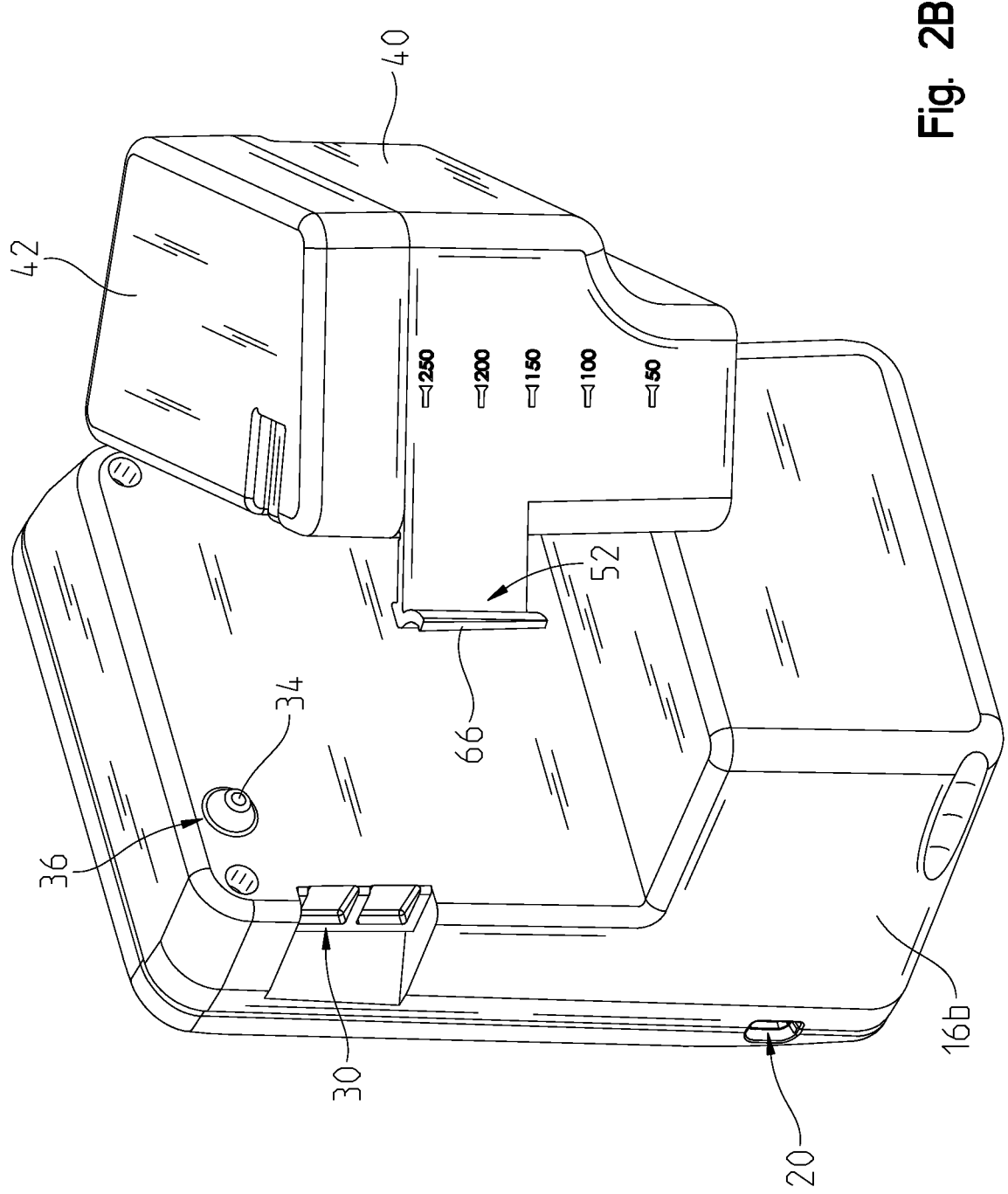
Figure 2C:
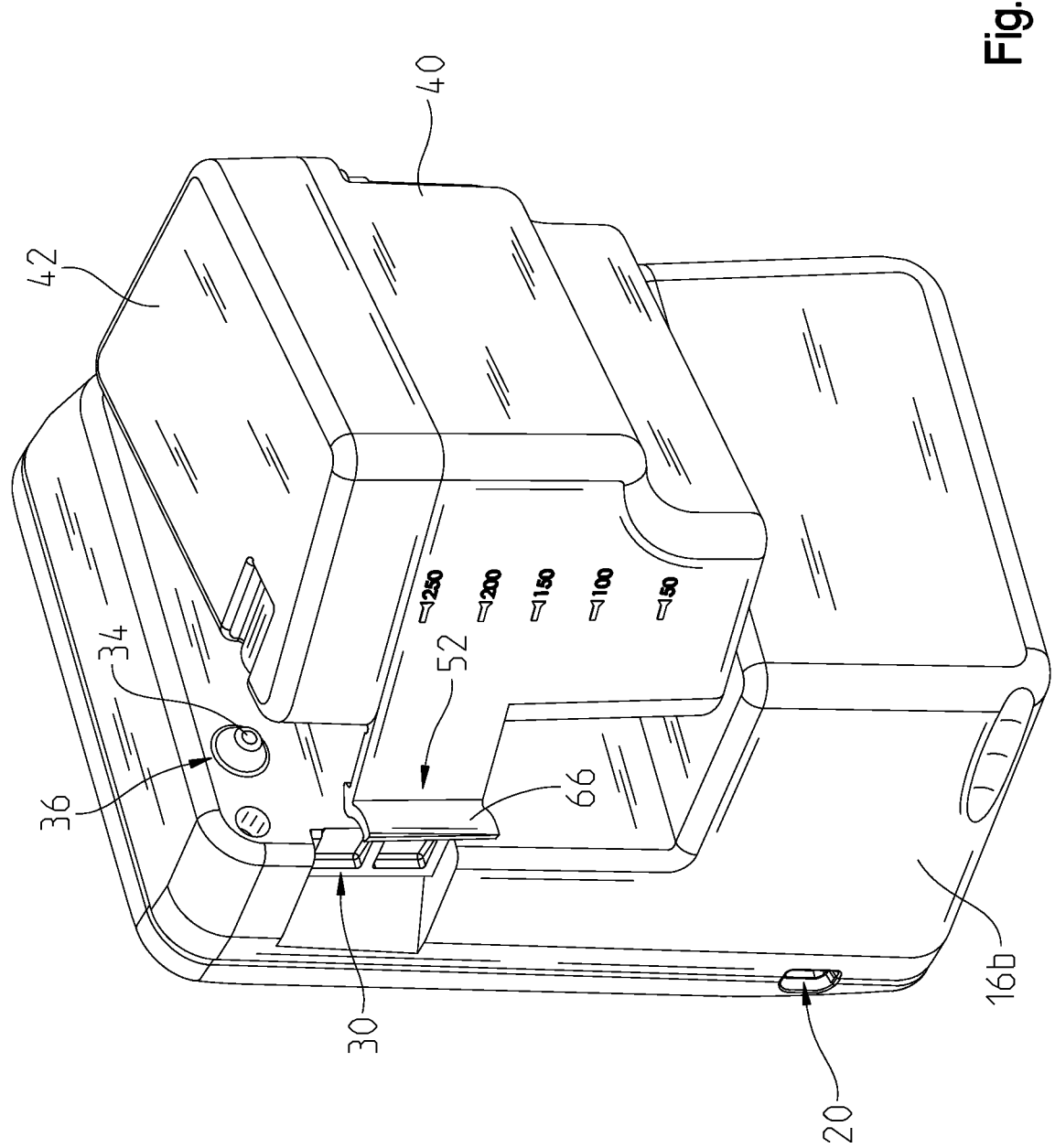
Figure 2D:
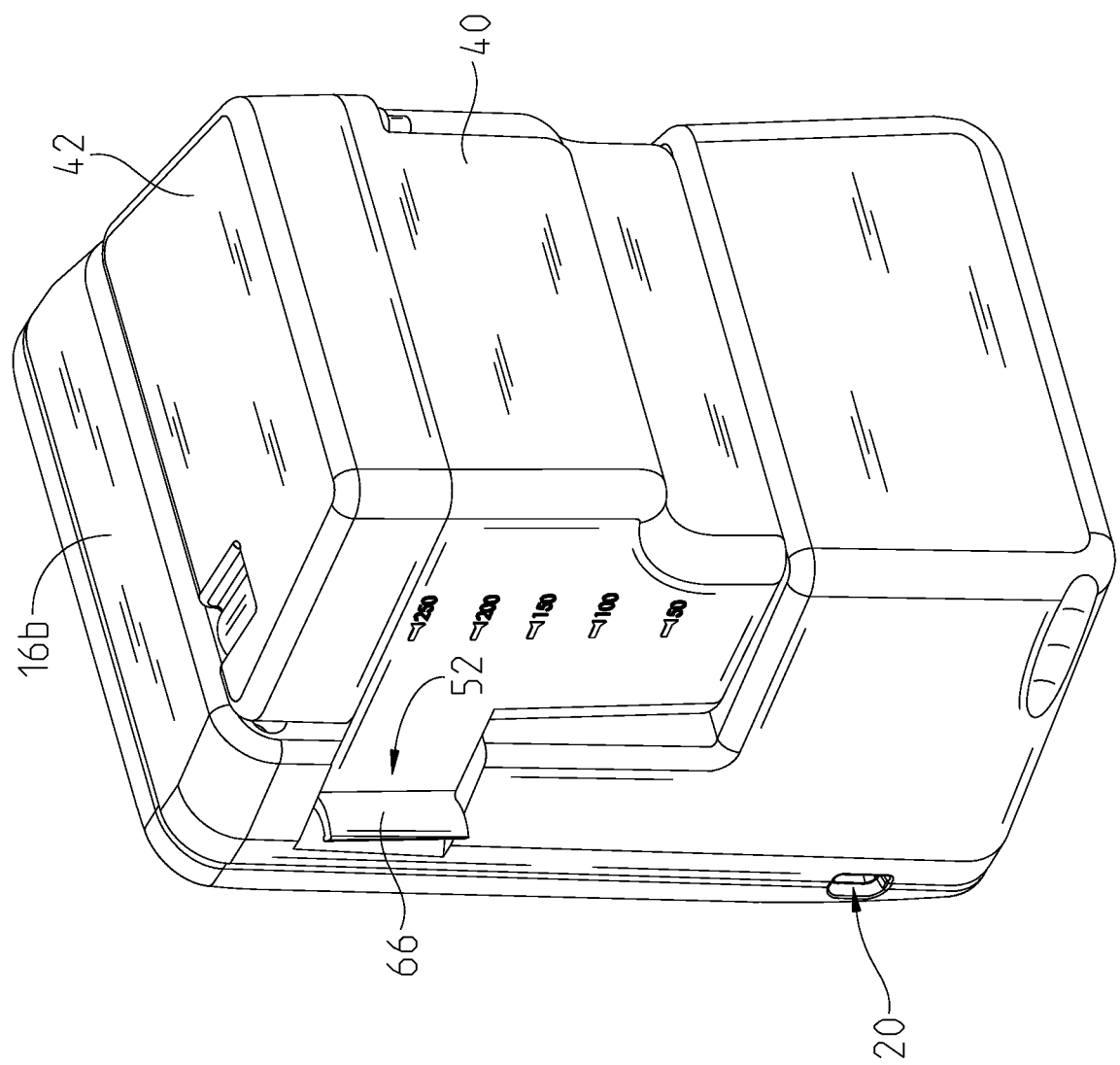
Figure 2E:
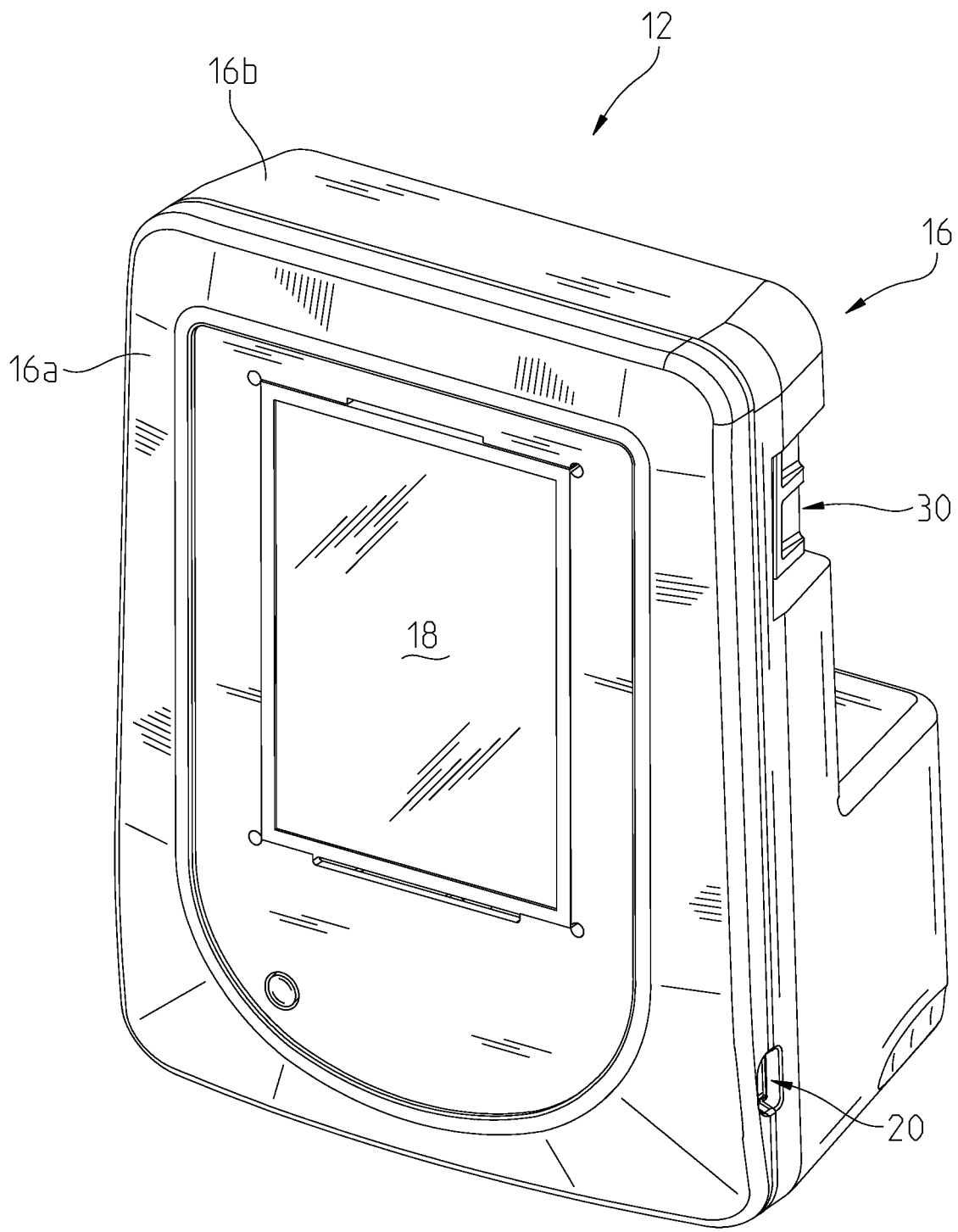
Figure 2F:
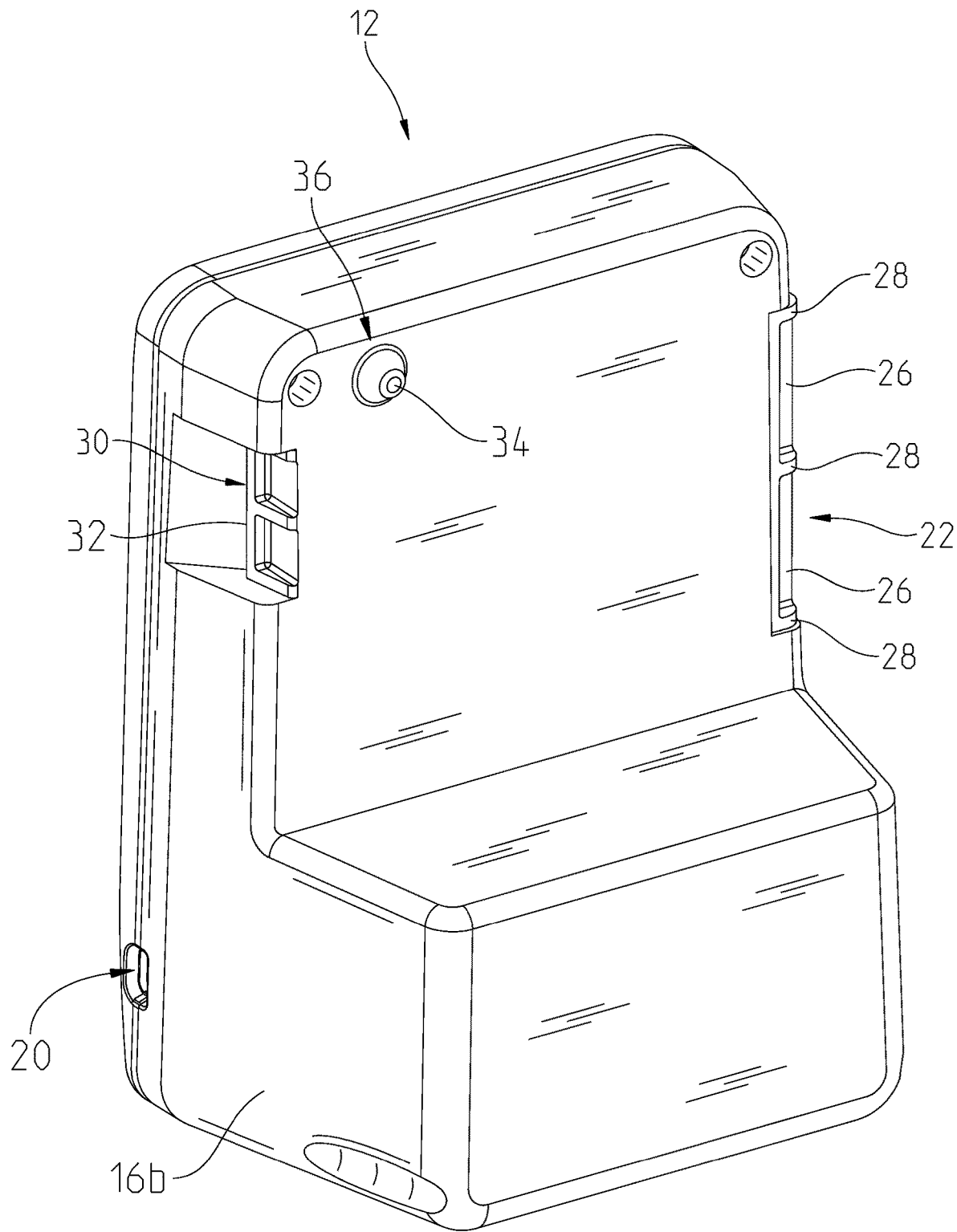
Figure 2G:
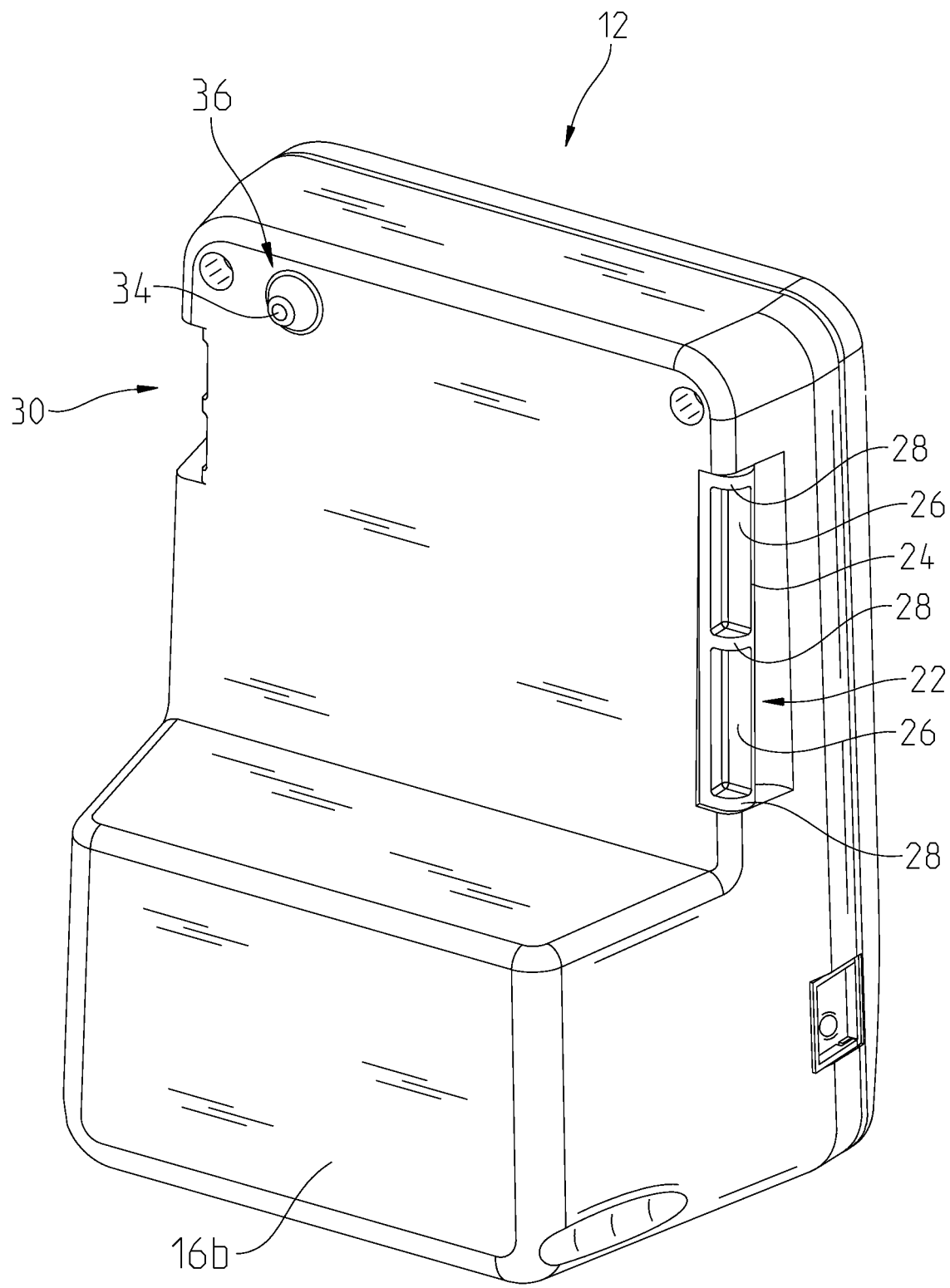
Figure 3A:
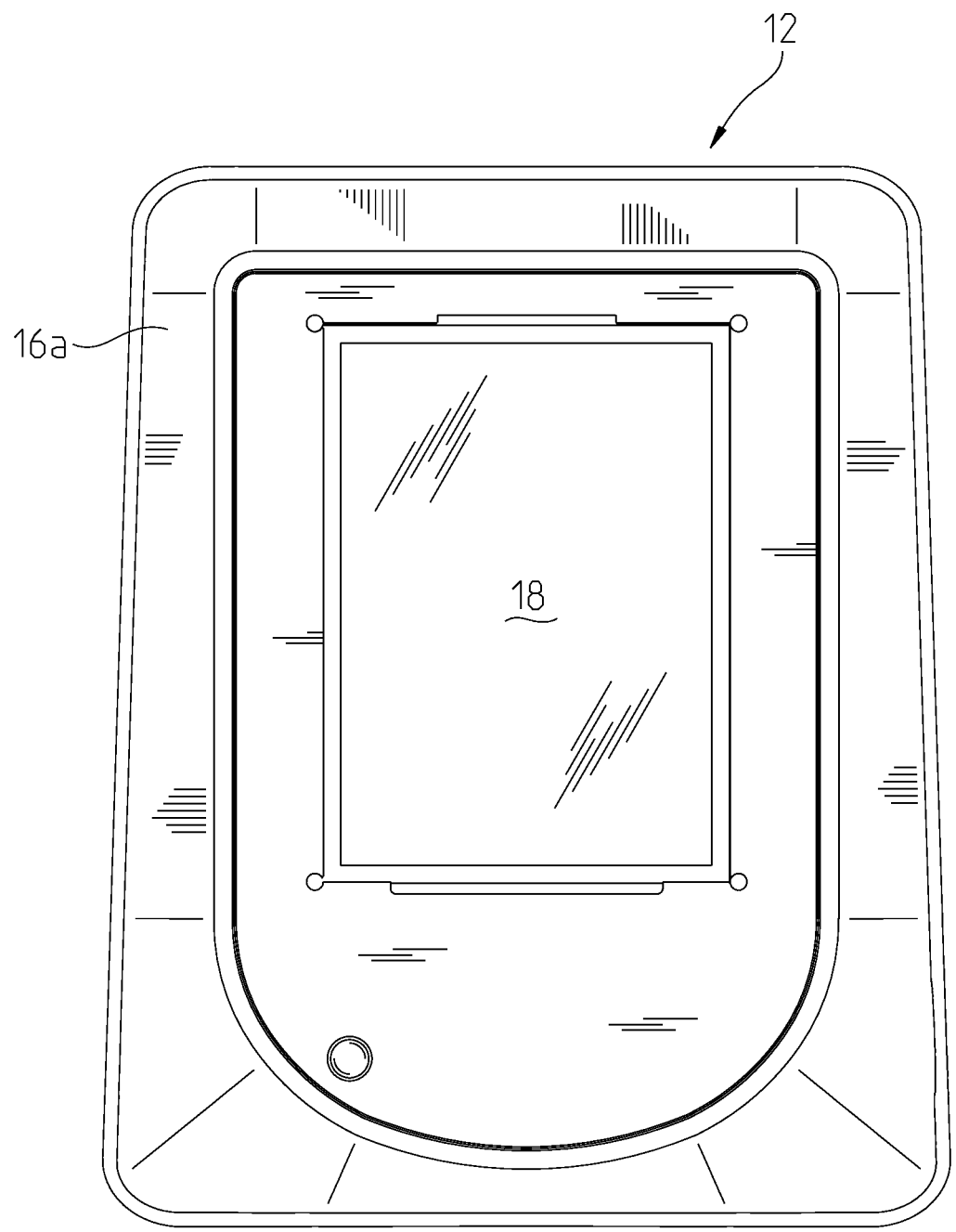
FIGS. 3A-F are plan views of the pump of FIG. 1.
Figure 3B:
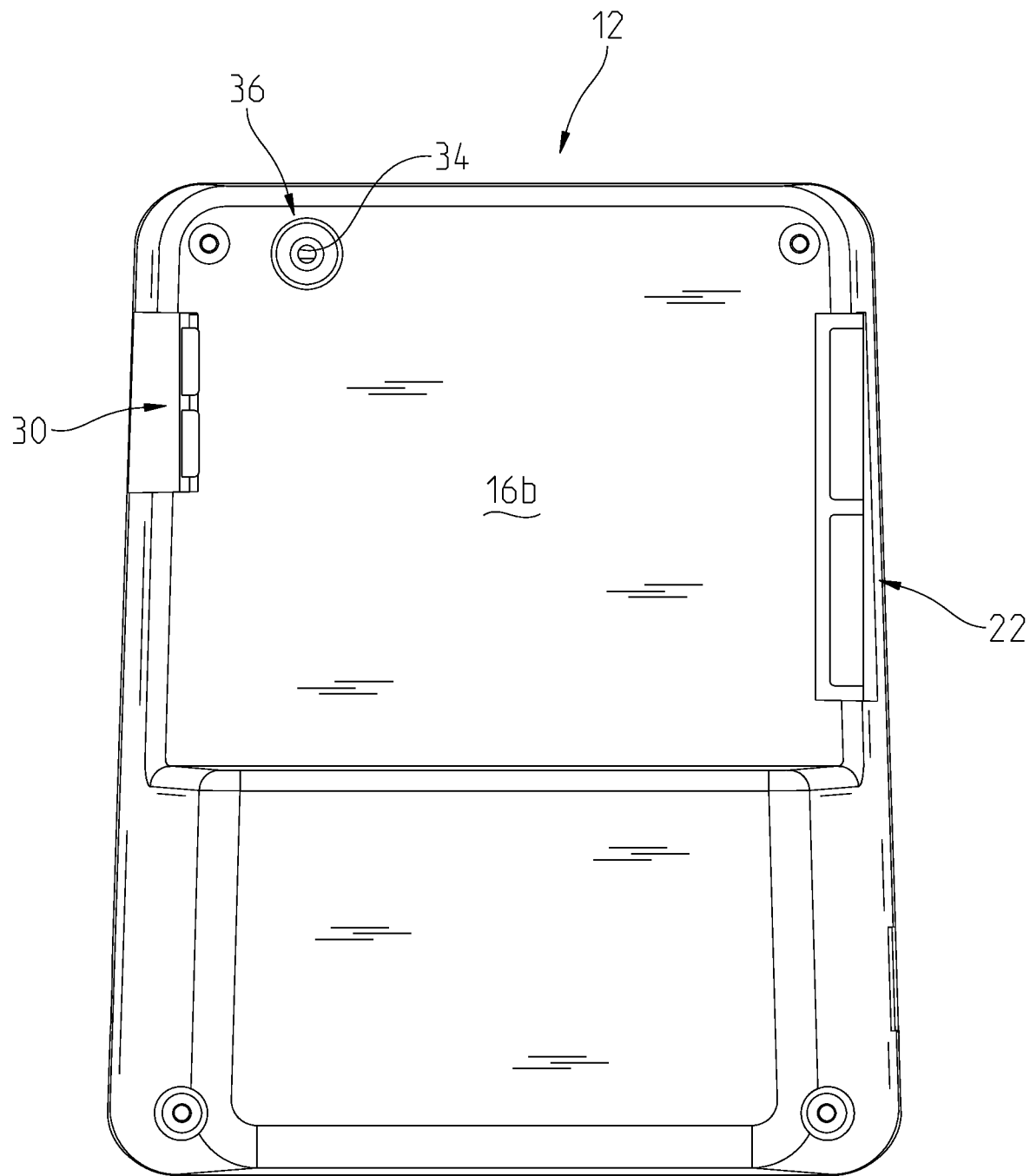
Figure 3C:
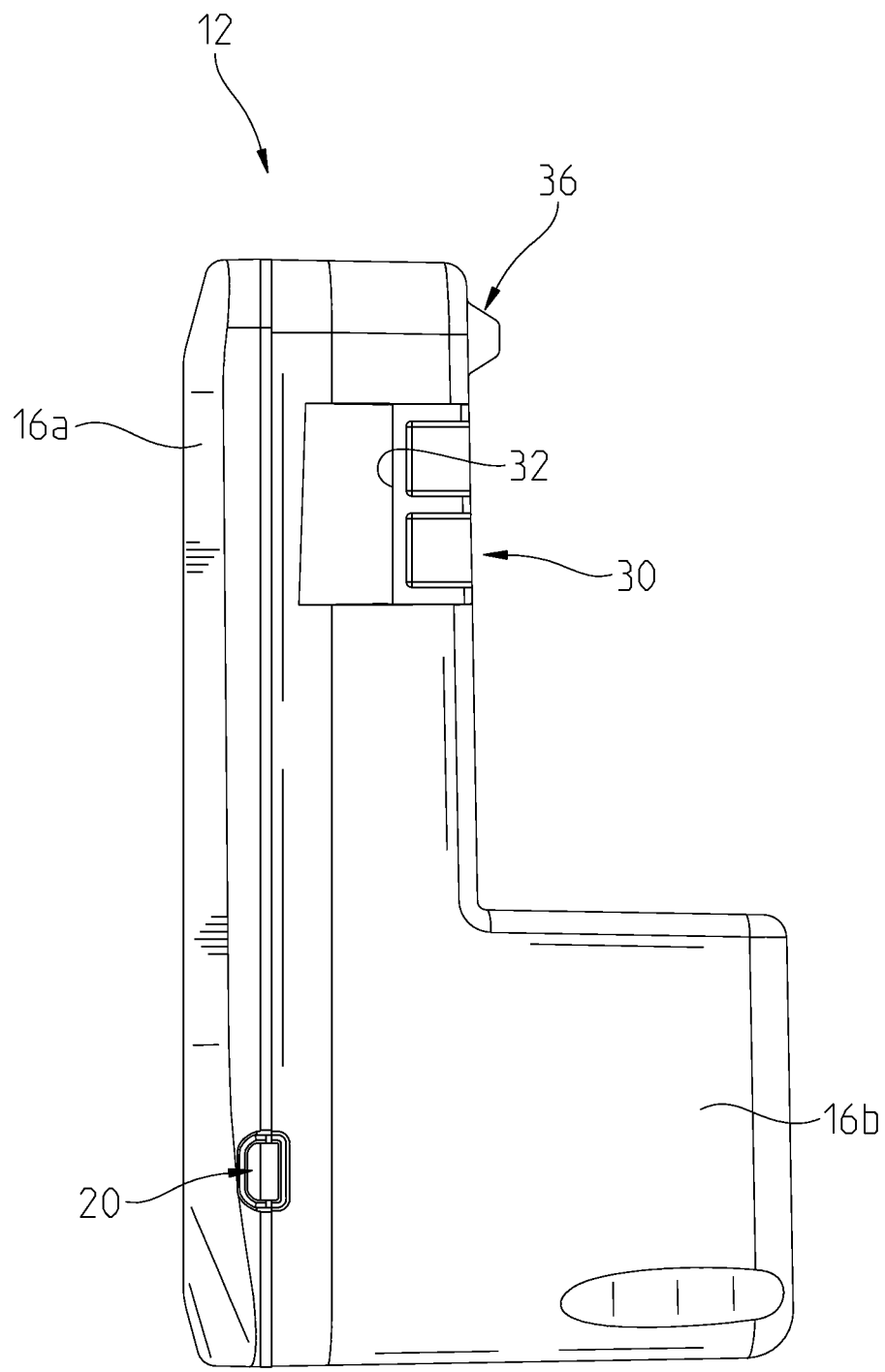
Figure 3D:
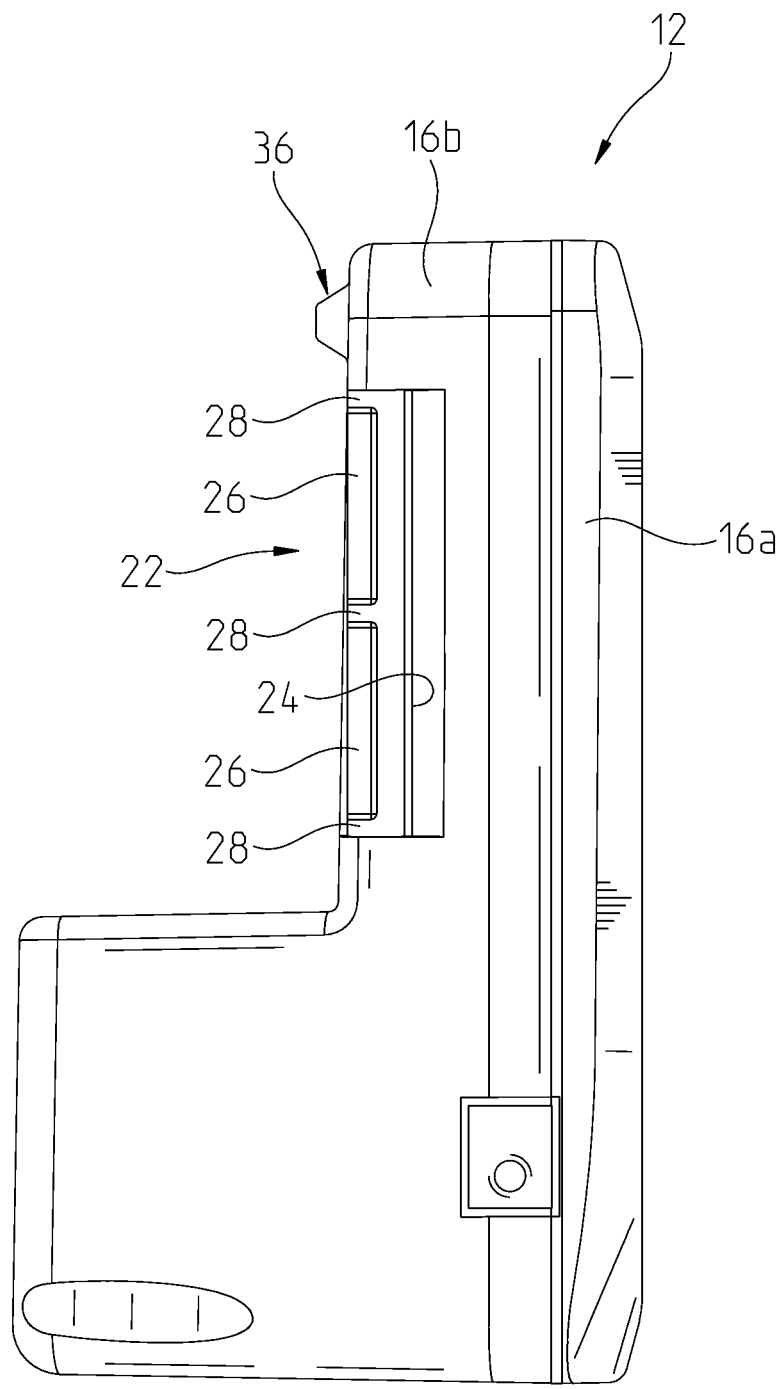
Figure 3E:
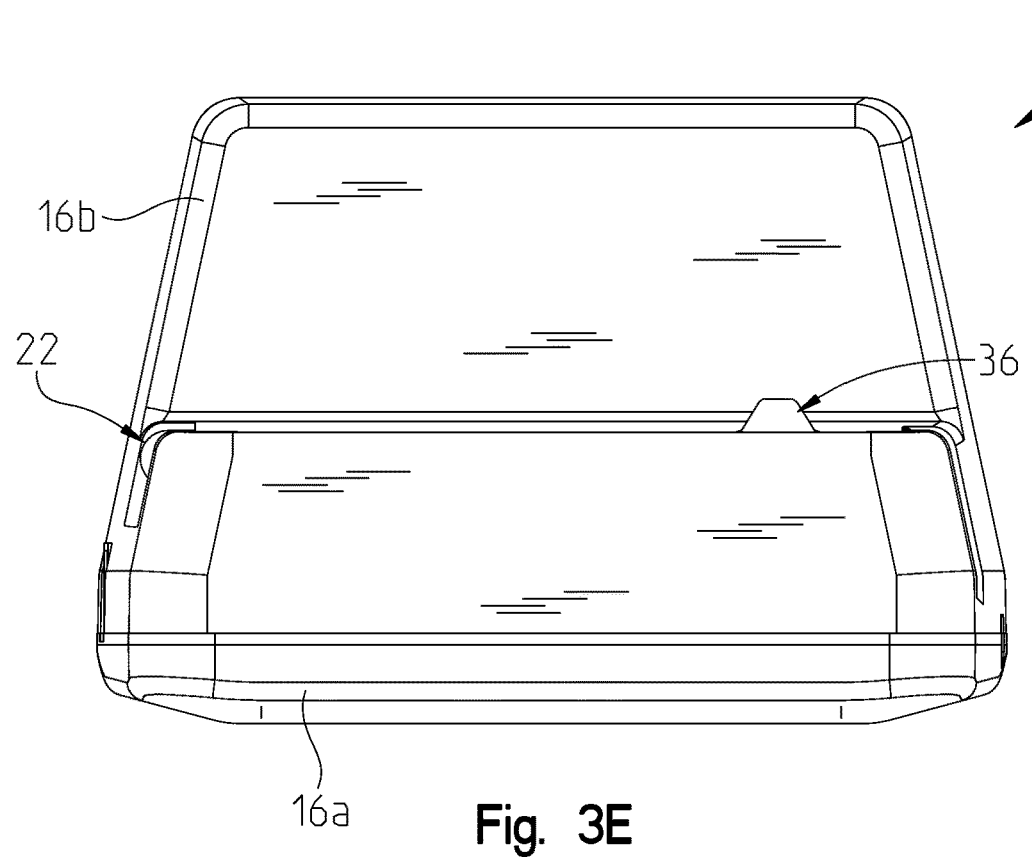
Figure 3F:
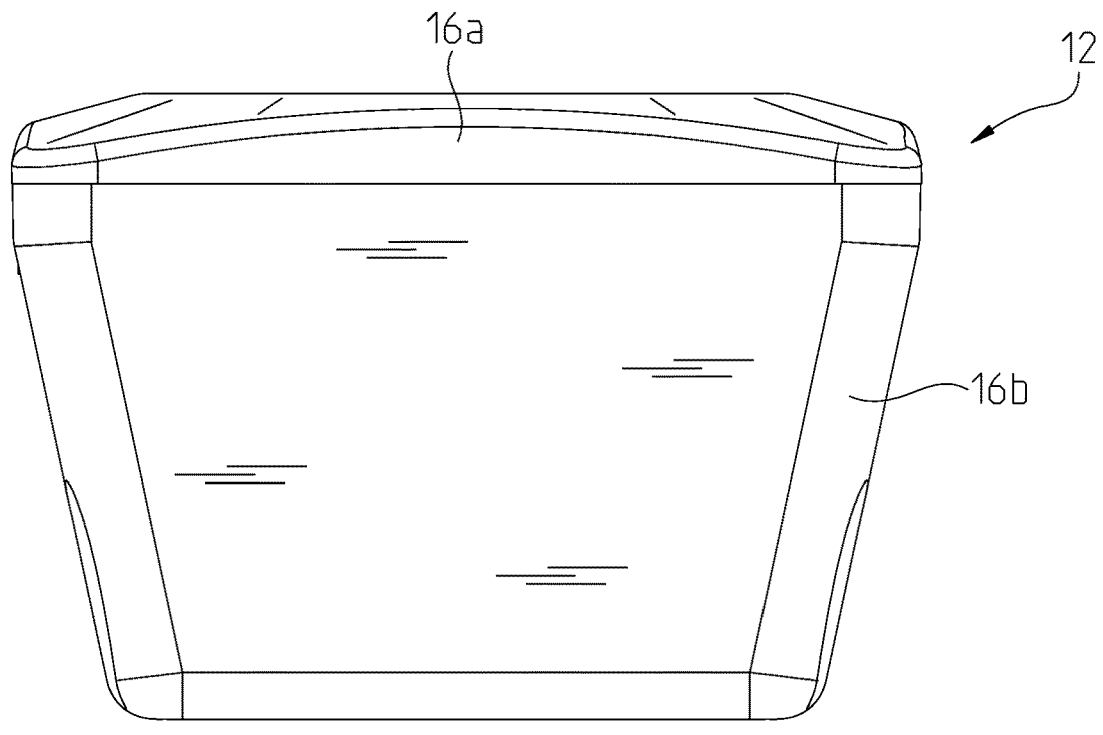
Figure 4:
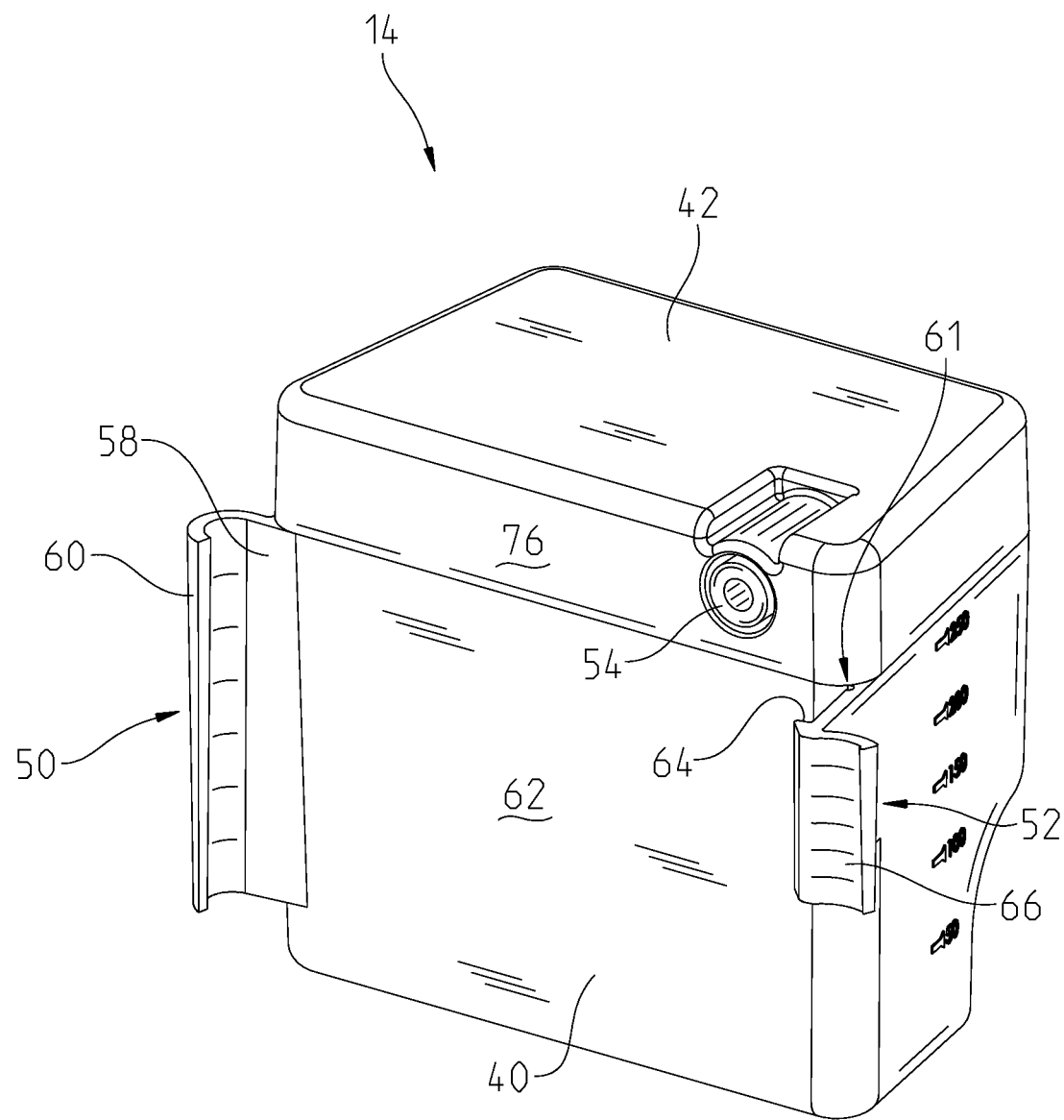
FIG. 4 is a perspective view of the first embodiment canister of FIG. 1.
Figure 5A:
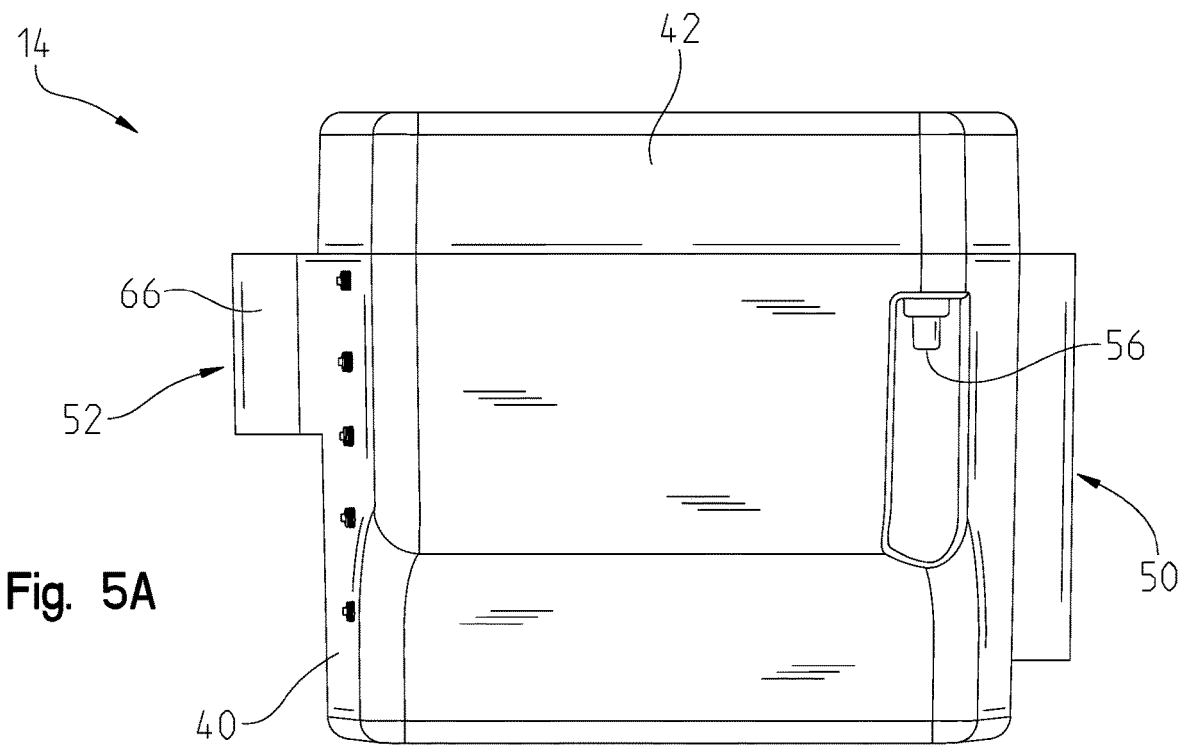
FIGS. 5A-F are plan views of the first embodiment canister of FIG. 1.
Figure 5B:
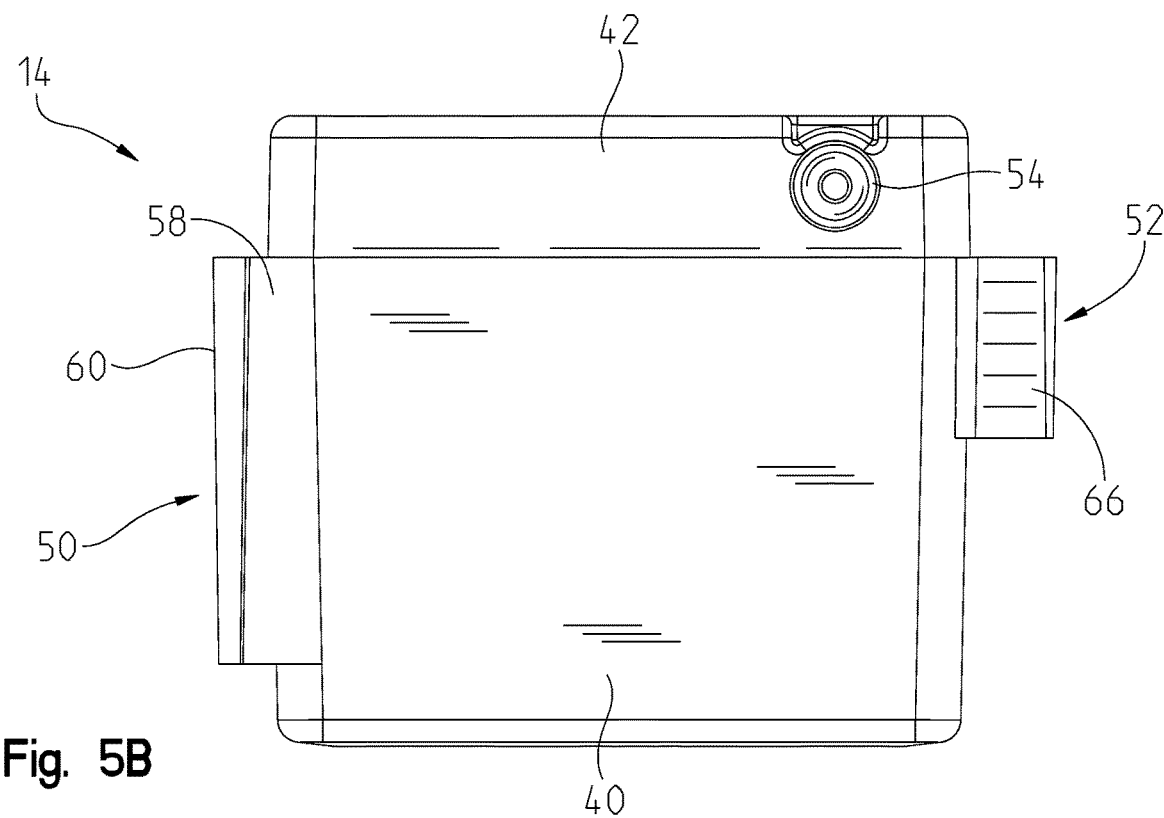
Figure 5D:
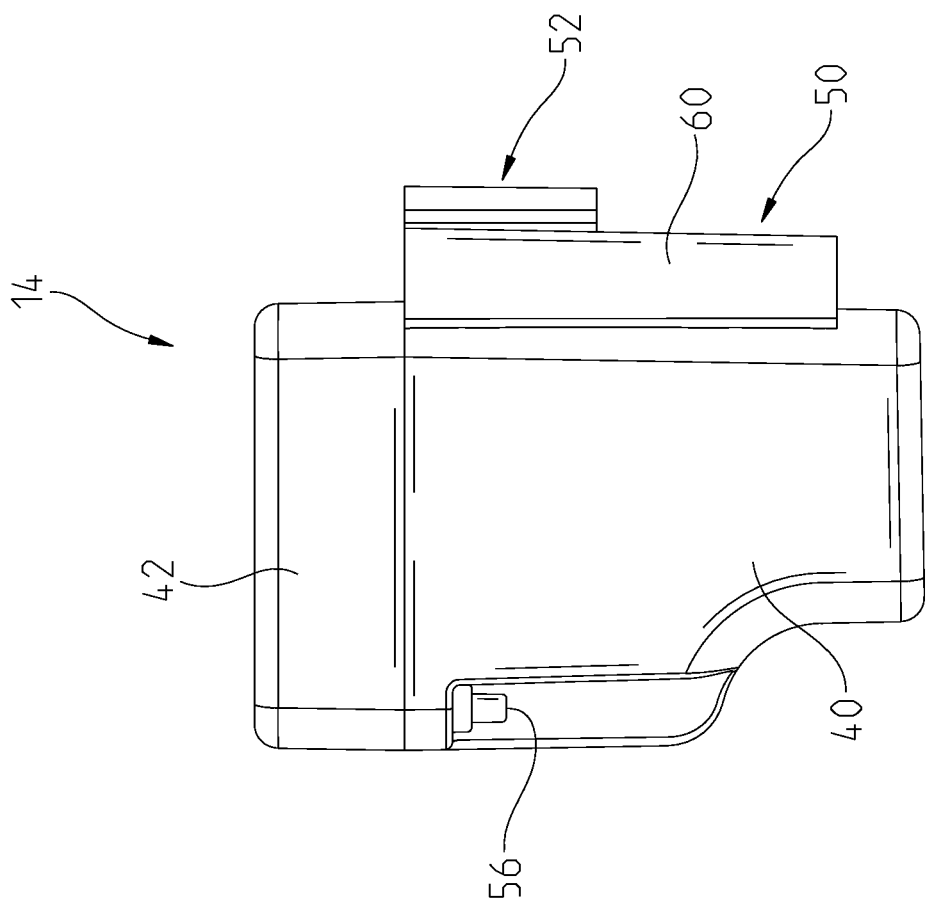
Figure 5C:
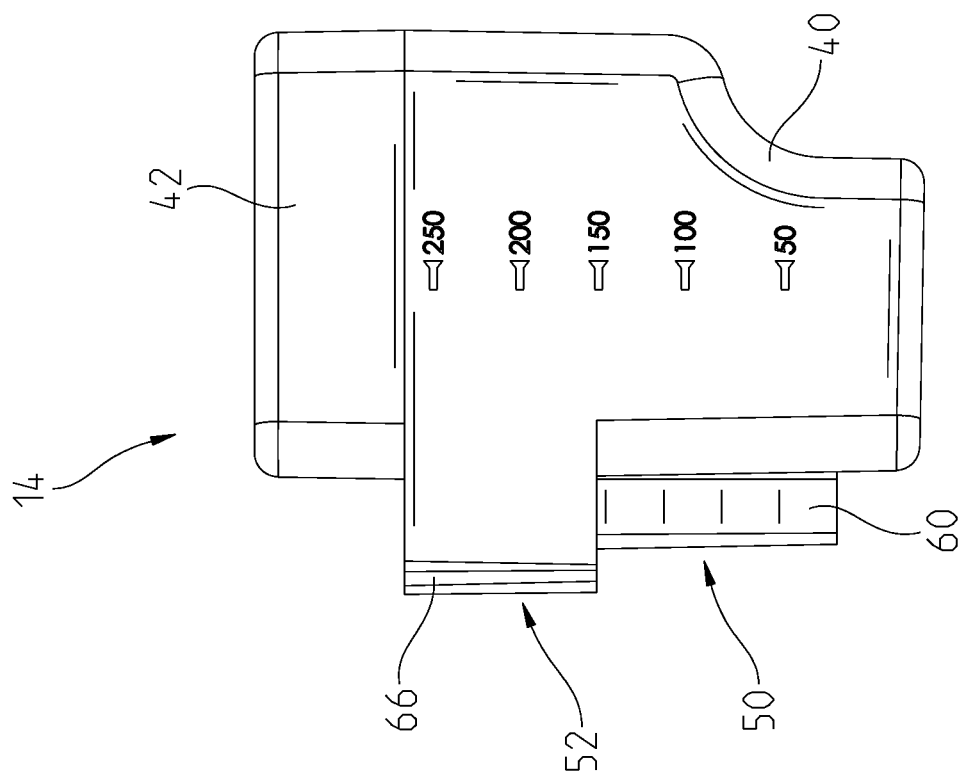
Figure 5E:
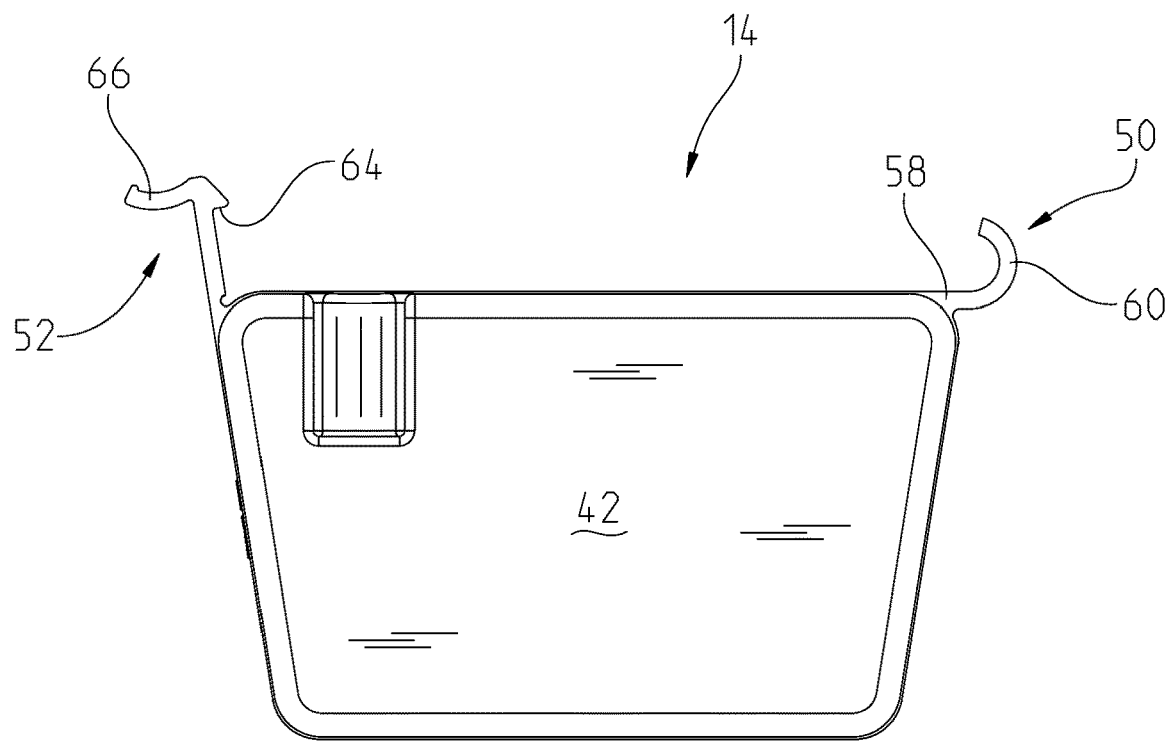
Figure 5F:
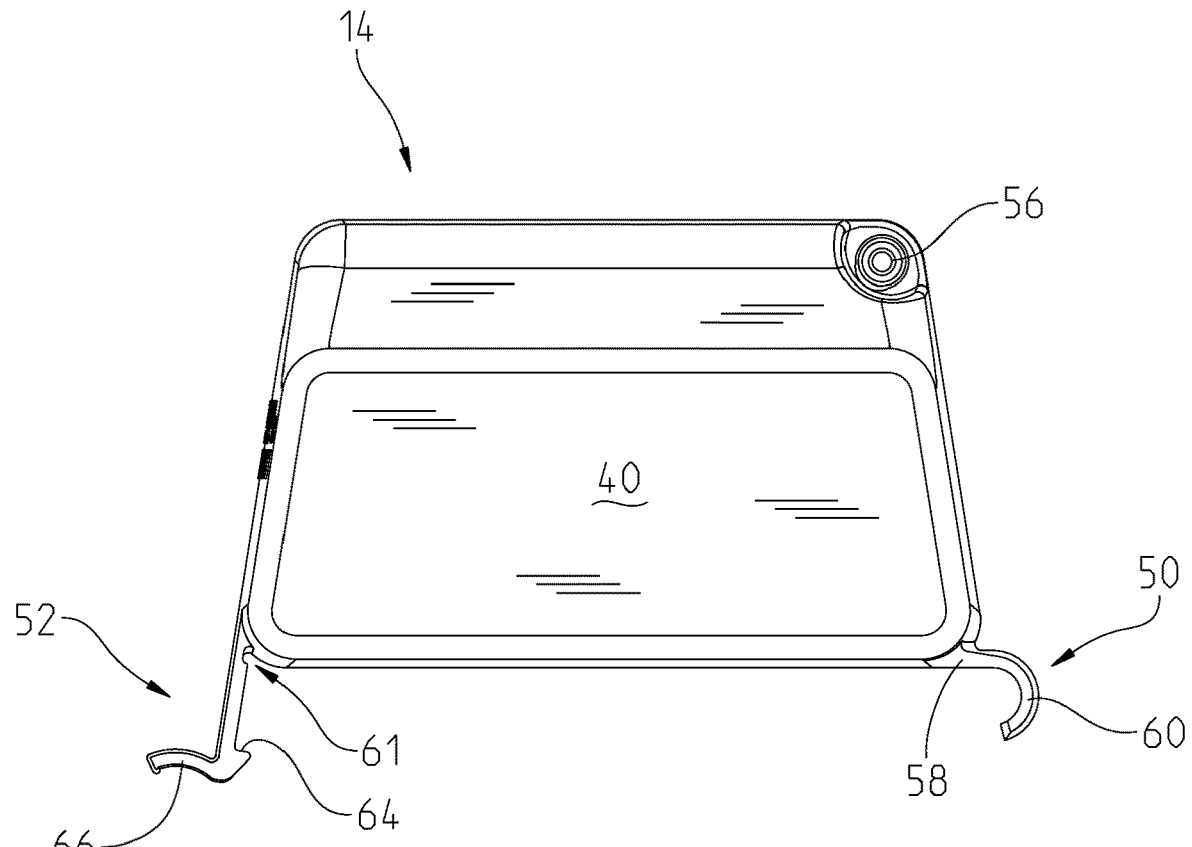
Figure 6:
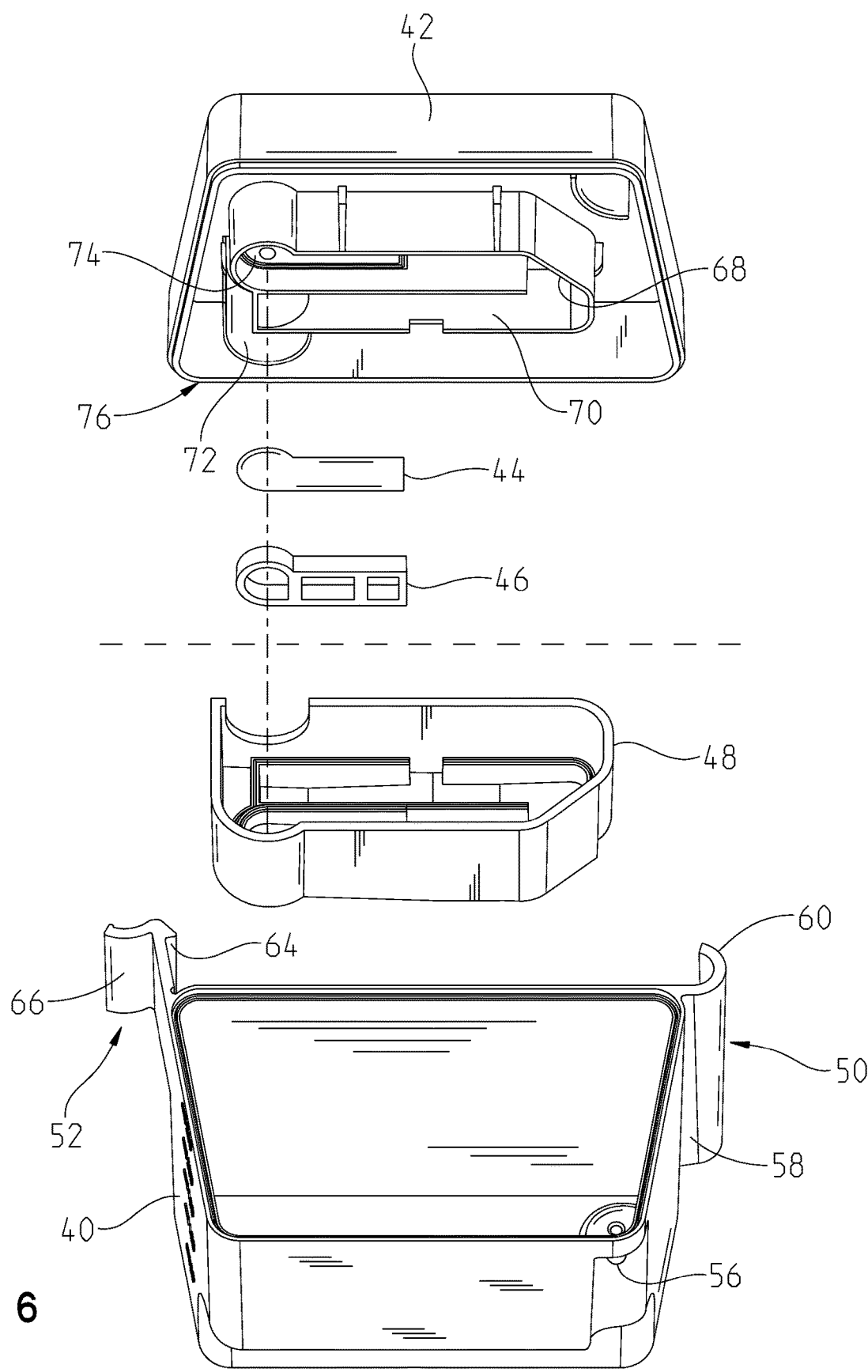
FIG. 6 is an exploded view of the canister of FIG. 1.
Figure 7:
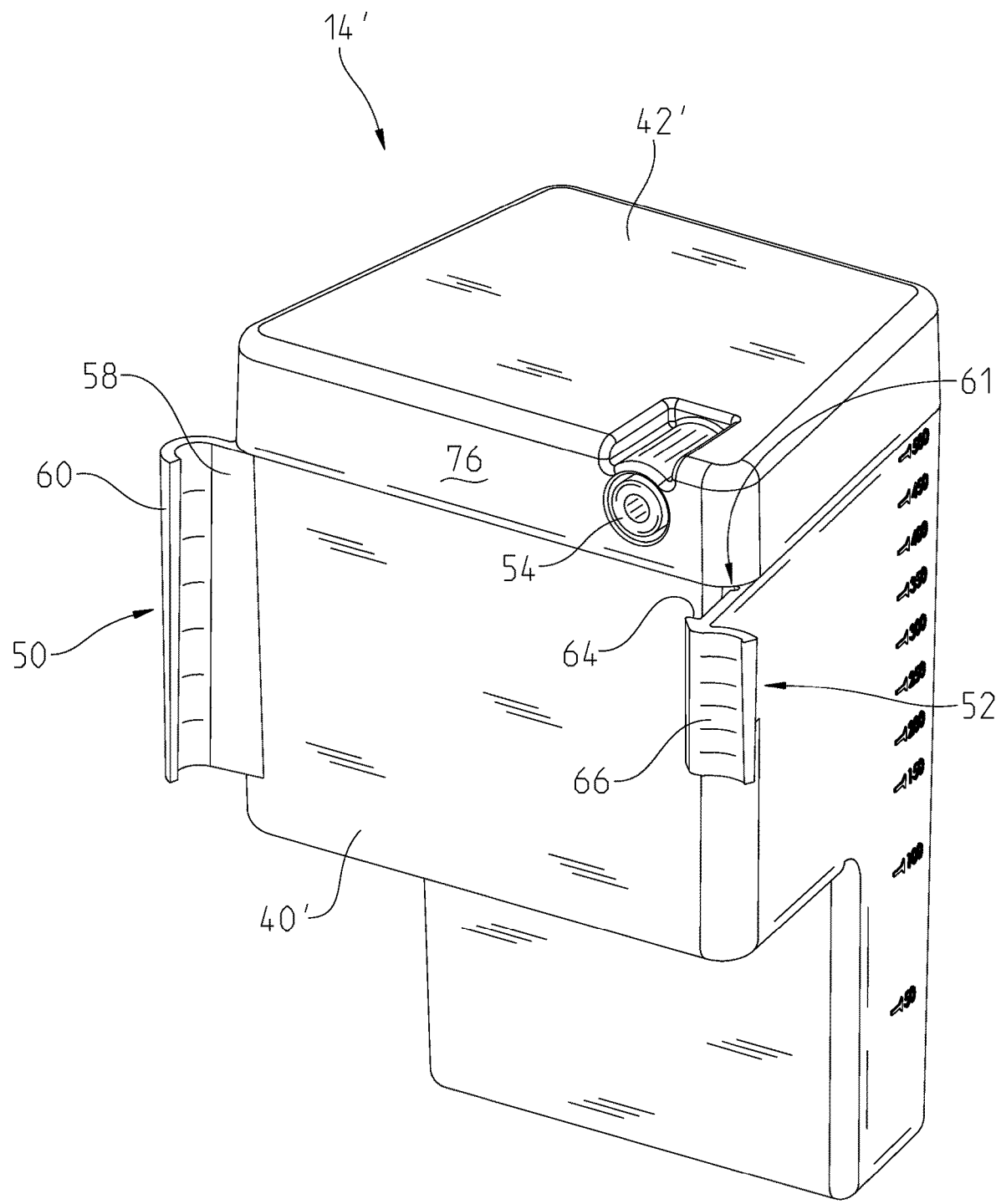
FIG. 7 is a perspective view of a second embodiment canister.
Figure 8A:
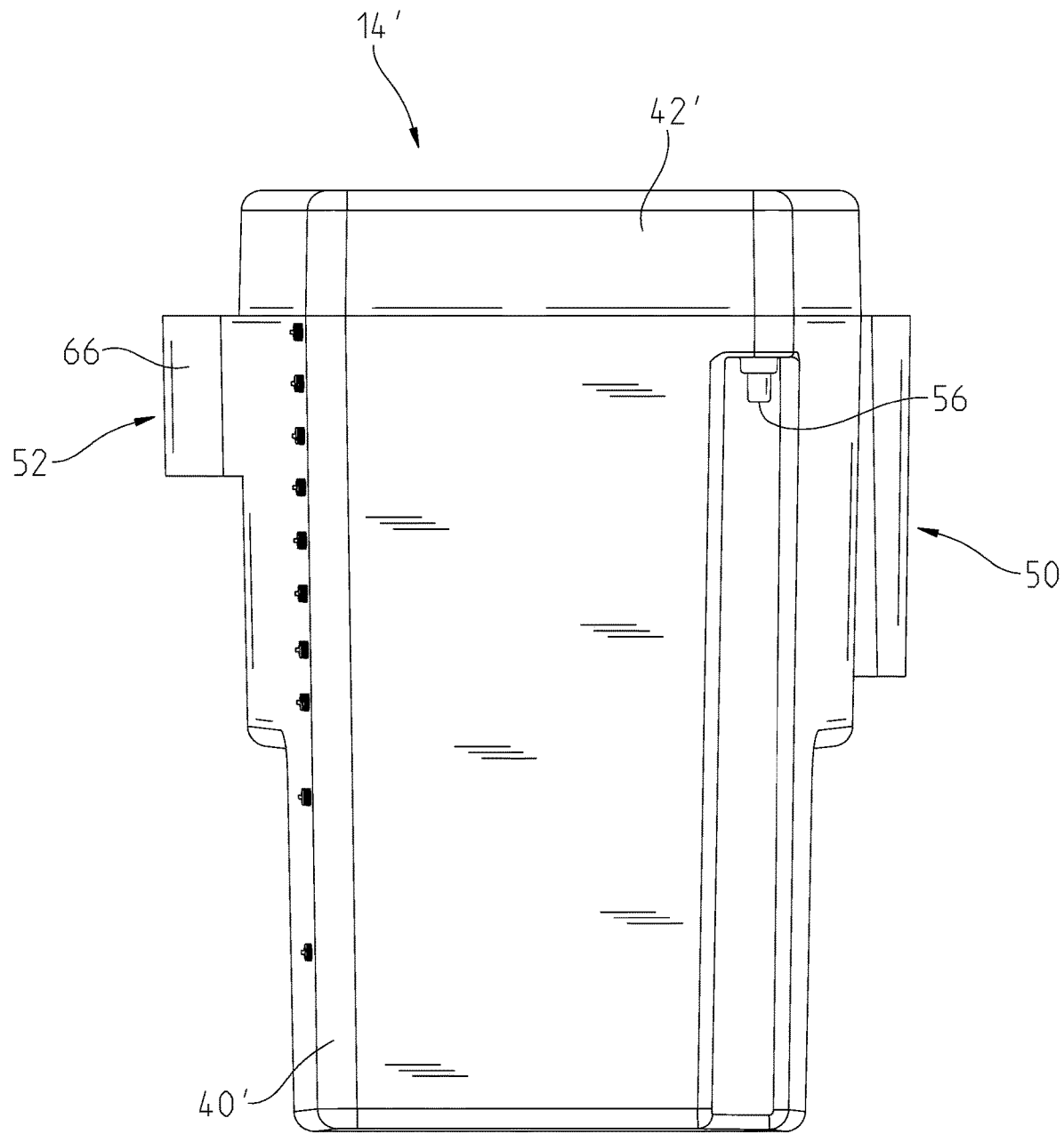
FIGS. 8A-F are plan views of the second embodiment canister of FIG. 8.
Figure 8B:
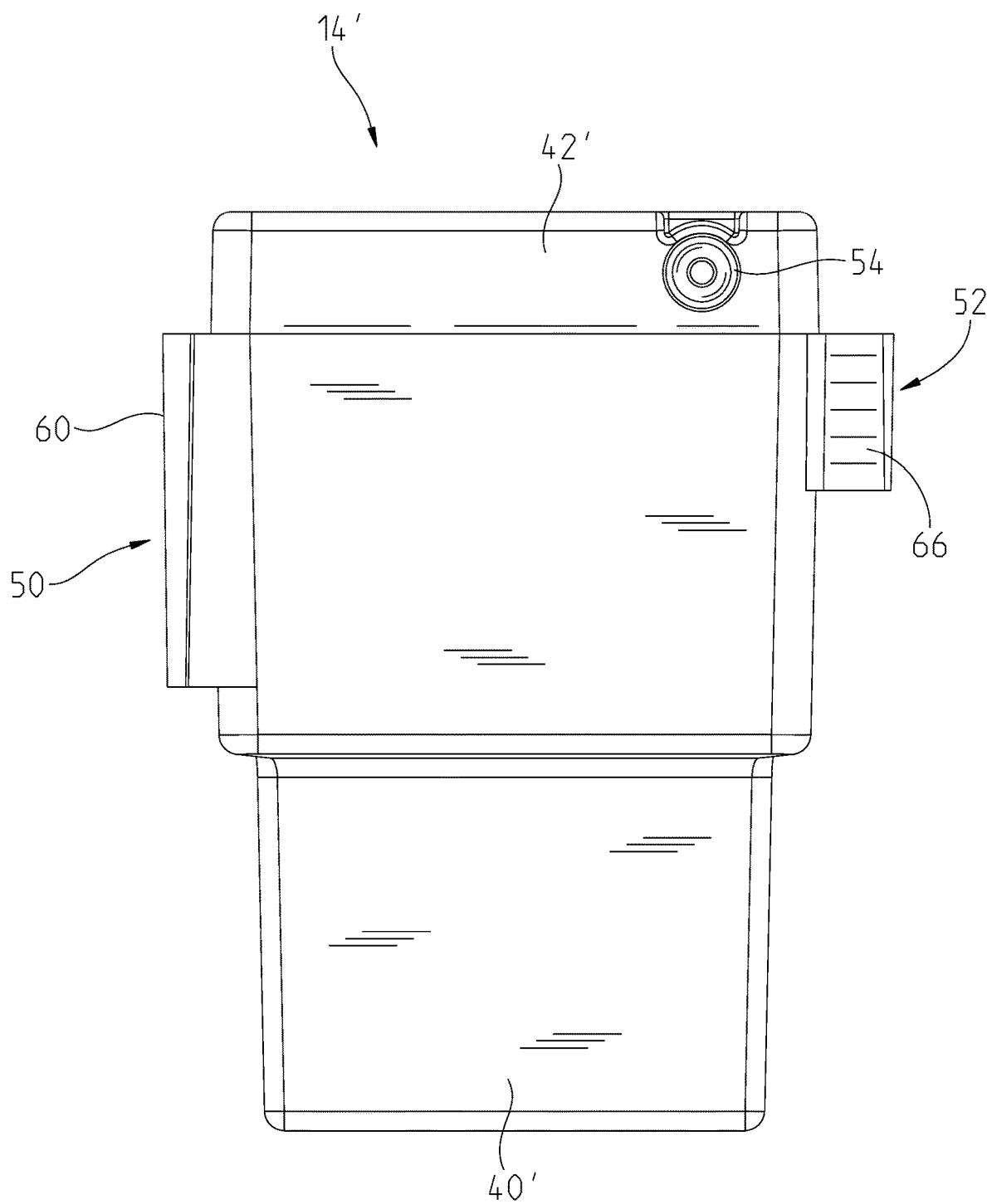
Figure 8C:
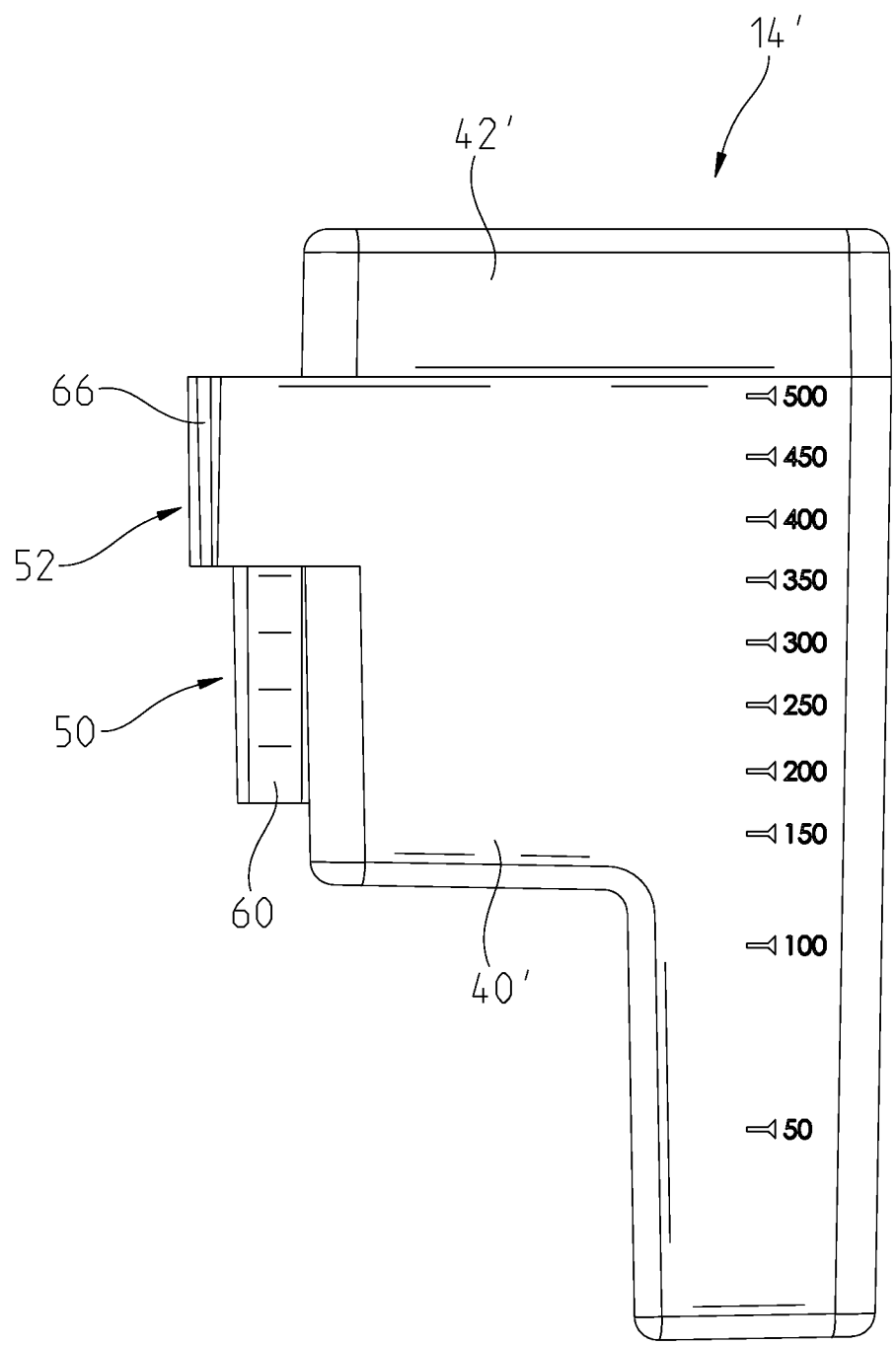
Figure 8D:
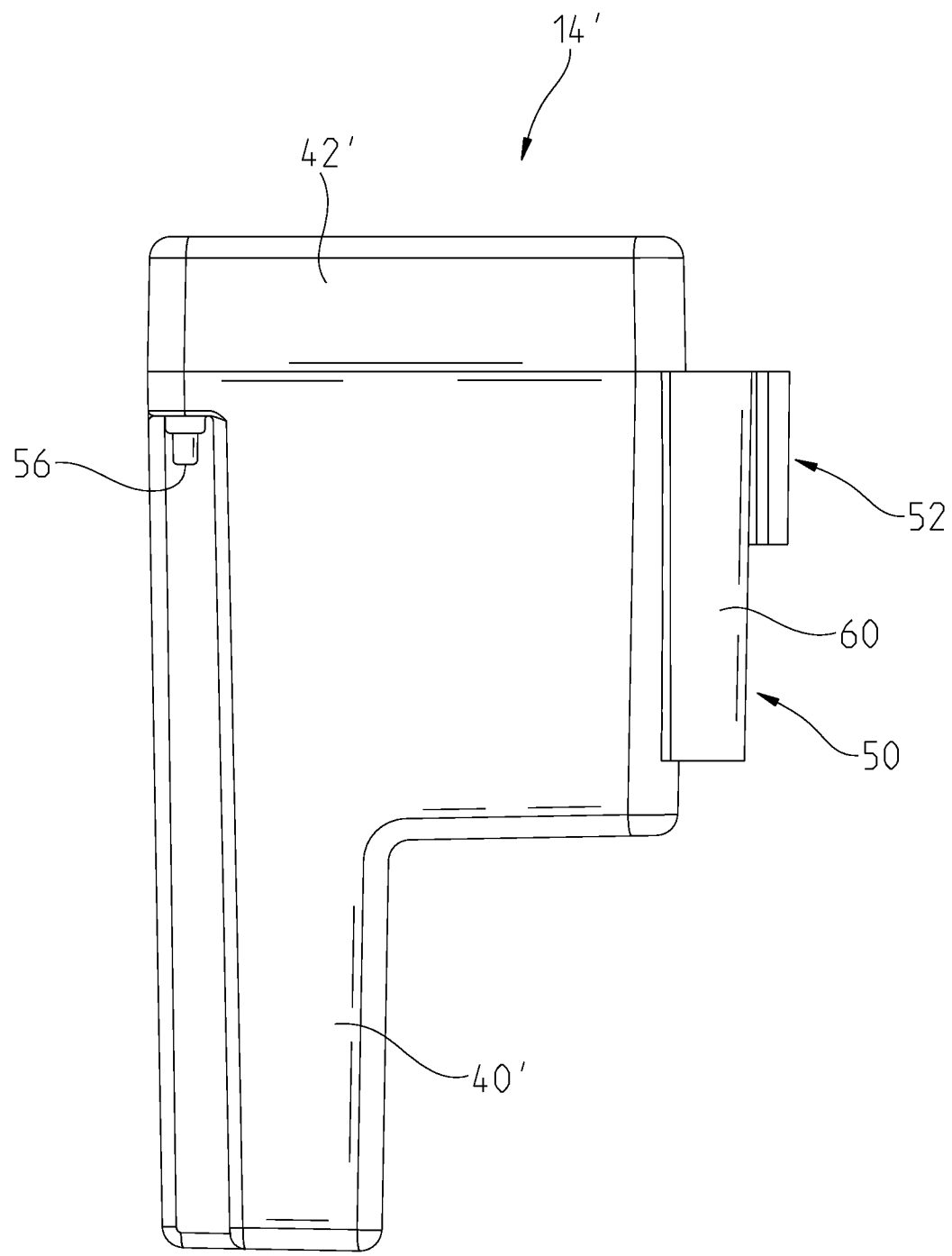
Figure 8E:
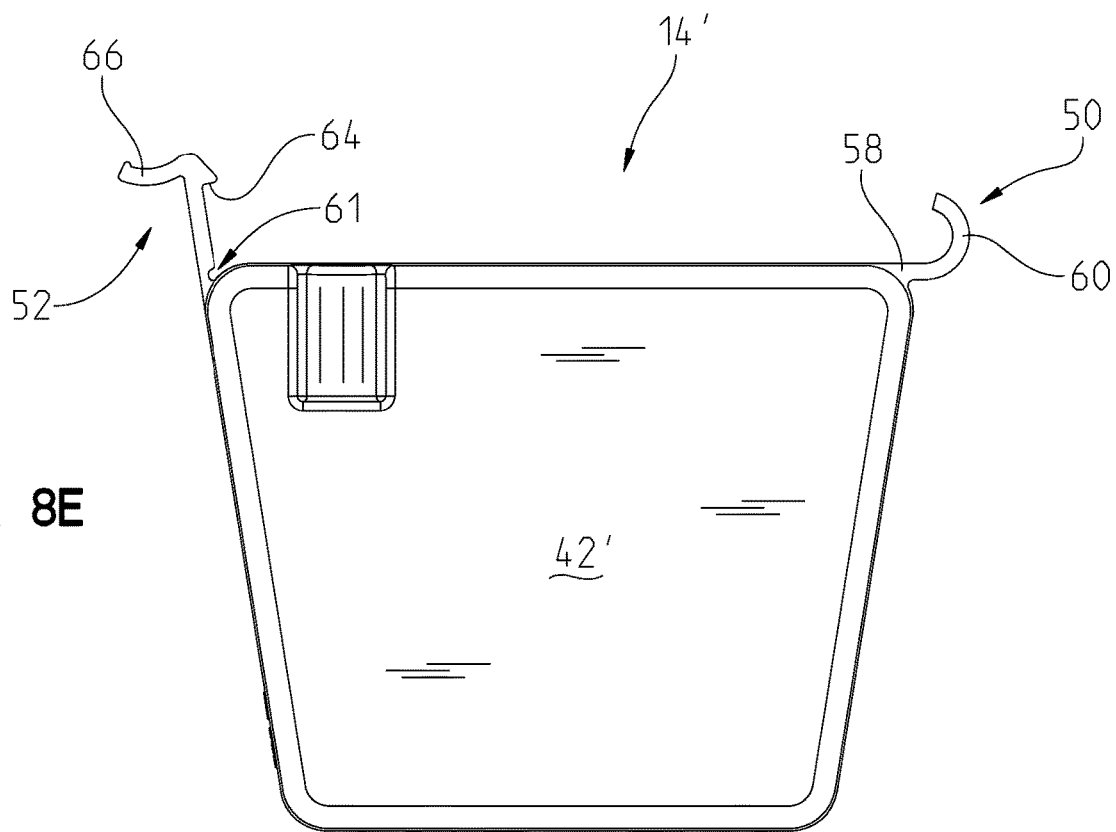
Figure 8F:
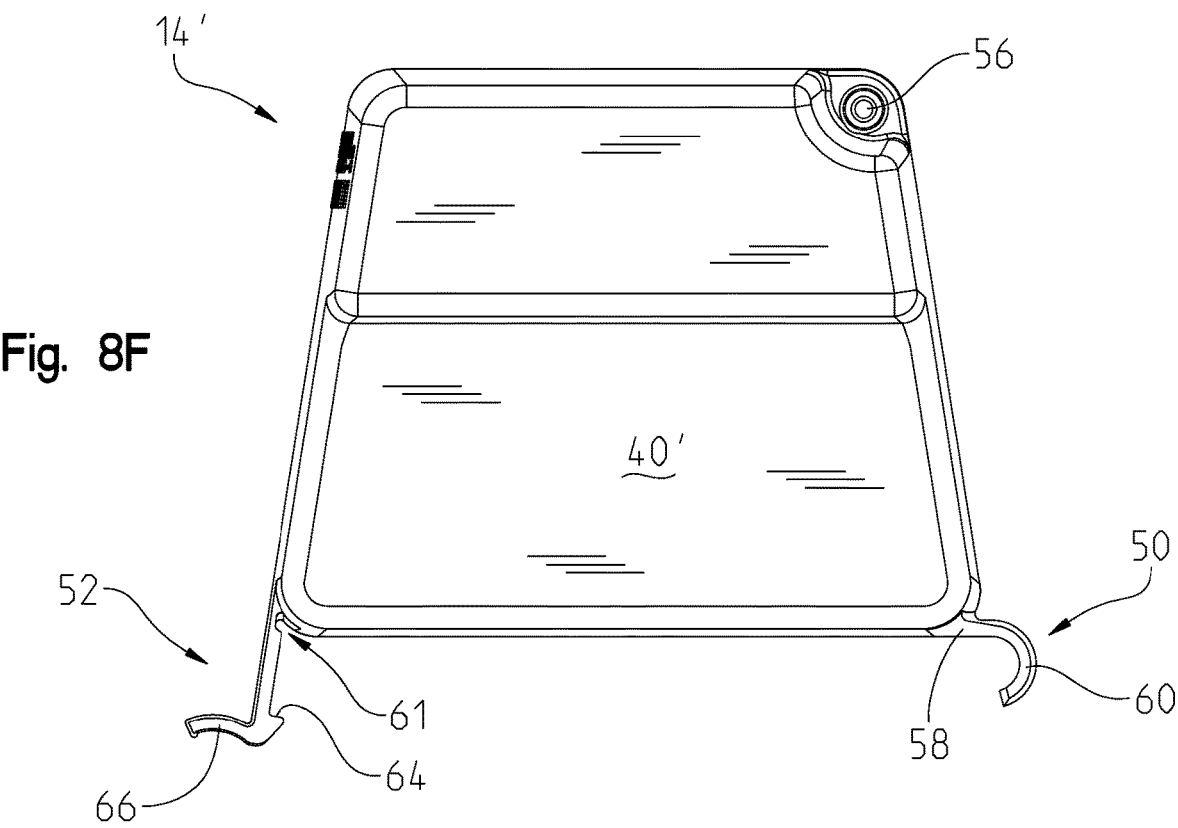

To couple canister 14, 14' to pump apparatus 12, canister 14, 14' is held at an angle as shown in FIGS. 2A-B. The exact angle shown in FIGS. 2A-B is not critical, but rather any angle is suitable such that the open side of hinge knuckle portion 50 is able to receive hinge pin 22 therein. Once hinge pin 22 is within knuckle portion 50, canister 14, 14' is rotated clockwise (FIG. 2C) until latch 52 abuts a portion of latch catch 30. Further clockwise movement of canister 14, 14' causes flexing of latch 52 to allow the backside of shoulder 64 to ride over the backside of shoulder 32 until shoulder 64 passes shoulder 32. At such point, latch 52 snaps back inward so that shoulder 32 and shoulder 64 abut one another and hold canister 14, 14' in engagement with each other (FIG. 2D). Thus, on one lateral side of device 10, the interface of shoulders 32, 64 hinder disengagement of canister 14, 14' and housing 16. On the opposite lateral side, the interface of forward facing wall 24 and a portion of hinge knuckle portion 50 hinder disengagement of canister 14, 14' and housing 16. Canister 14, 14' is thus securely mounted to housing 16.

It should be appreciated that this mounting of canister 14, 14' to housing 16 further causes abutment of tubular conduit 54 to conduit seat 36. In one embodiment, mounting of canister 14, 14' to housing 16 abuts tubular conduit 54 to conduit seat 36 such that tubular conduit 54 is at least slightly longitudinally compressed. Furthermore, while the location of tubular conduit 54 and conduit seat 36 are designed to align, the frusto-conical shape of conduit seat 36 allows for some positioning error and serves to re-center tubular conduit 54 on conduit seat 36. Still further, negative pressure is being supplied to tubular conduit 54. Accordingly, due to the pliable nature of tubular conduit 54, negative pressure therein serves to at least somewhat pull interior walls of tubular conduit 54 into engagement with the frusto-conical surface of conduit seat 36. Pressure from the pump pulls the flexible conduit 54 into engagement with the pump housing 16b. Accordingly, the pliability and frusto-conical shape provide for a seal of the interface with housing 16 and the biasing provided by negative pressure only serves to enhance that seal. The frusto-conical shape of conduit seat 36 also aids in minimizing liquid intrusion into housing 16. While membrane 44 and other elements discussed herein aid in minimizing liquid in canister 14, 14' from exiting via tubular conduit 54, the medical environment, including the cleaning process for pump 12 may involve liquids. Accordingly, as noted the shape of conduit seat 36 aids in reducing the likelihood of any fluids that come into contact with housing 16 from being deposited within the output port 34.

It should also be appreciated that the location of tubular conduit 54 on an opposite lateral side from hinge pin 22 which serves as an axis of rotation for canister 14, 14' provides that, for the given setup, tubular conduit 54 approaches conduit seat 36 in as close to a straight line as possible.

When the canister is full or it is otherwise desired that canister 14, 14' be removed from housing 16, release 66 of latch 52 is urged away from housing 16 such that shoulder 32 and shoulder 64 disengage and latch 52 gains clearance of shoulder 32 such that housing 16 can be rotated counter-clockwise relative to canister 14, 14'. Once latch 52 has lateral clearance of housing 16, canister 14, 14' can be moved laterally so as to remove hinge pin 22 from within hinge knuckle portion 50.

The above detailed description and the examples described therein have been presented for the purposes of illustration and description only and not for limitation. For example, the operations described may be done in any suitable manner. The method steps may be done in any suitable order still providing the described operation and results. It is therefore contemplated that the present embodiments cover any and all modifications, variations or equivalents that fall within the spirit and scope of the basic underlying principles disclosed above and claimed herein.

What is claimed is:

1. An apparatus including:
a negative pressure wound therapy pump portion including a pump housing; the pump housing defining a first hinge portion on a first lateral side, the pump housing further defining a latch catch on a second lateral side opposite the first side, the pump portion including a vacuum pump disposed within the pump housing; and
a canister sized and shaped to be selectively coupled to and readily removable from the pump portion, the canister including a second hinge portion, the first hinge portion and the second hinge portion hingedly coupleable through a hinged range of motion, the hinged range of motion including a tethered position in which the pump portion is tethered to the canister, the hinged range of motion further including an untethered position in which the canister is untethered from the pump portion to be readily removable from the pump portion, wherein in the untethered position of the hinged range of motion the second hinge portion of the canister is hingedly coupled to the first hinge portion of the pump portion and the second hinge portion is untethered to the first hinge portion, the canister further including a latch sized and shaped to engage the latch catch.

2. The apparatus of claim 1, wherein each of the first and second hinge portions are selected from the group including a hinge pin and a hinge knuckle.

3. The apparatus of claim 2, wherein the hinge knuckle is formed as a portion of a hollow cylinder.

4. The apparatus of claim 3, wherein the hollow cylinder knuckle includes a cylindrical wall that extends greater than 90-degrees of a circle but less than 360-degrees of a circle.

5. The apparatus of claim 1, wherein the latch is unitary with a wall of the canister.

6. The apparatus of claim 1, wherein the latch is constructed such that a force administered to a distal portion of the latch when the latch is engaging the latch catch provides for the latch to flex relative to a wall of the canister and to move away from and disengage from the latch catch.

7. The apparatus of claim 6, wherein the canister is able to rotate about one of the first and second hinge portions when the latch is disengaged from the latch catch and is prevented from rotating about either of the first and second hinge portions when the latch is engaged with the latch catch.

* * * * *